US006034218A

United States Patent [19]
Reed et al.

[11] Patent Number: 6,034,218
[45] Date of Patent: Mar. 7, 2000

[54] COMPOUNDS AND METHODS FOR IMMUNOTHERAPY AND IMMUNODIAGNOSIS OF PROSTATE CANCER

[75] Inventors: Steven G. Reed, Bellevue; Davin C. Dillon, Redmond; Daniel R. Twardzik, Bainbridge Island; Jennifer L. Mitcham, Redmond, all of Wash.

[73] Assignee: Corixa Corporation, Seattle, Wash.

[21] Appl. No.: 08/946,026

[22] Filed: Oct. 7, 1997

Related U.S. Application Data

[63] Continuation-in-part of application No. 08/633,840, Apr. 11, 1996, abandoned, which is a continuation-in-part of application No. 08/616,745, Mar. 15, 1996, abandoned.

[51] Int. Cl.[7] .................................................. C07K 14/00
[52] U.S. Cl. ..................... 530/350; 530/387.1; 536/23.1; 514/2; 435/4; 424/185.1
[58] Field of Search ........................... 536/23.1; 530/350, 530/387.1; 514/2; 435/4; 424/185.1

[56] References Cited

FOREIGN PATENT DOCUMENTS

| WO 90/09446 | 8/1990 | WIPO . |
| WO 94/09820 | 5/1994 | WIPO . |
| WO 95/04548 | 2/1995 | WIPO . |

OTHER PUBLICATIONS

Tubiana, M. J. Cancer Res Clin Oncol (Germany) 117 (4): 275–89, 1991.

Alkema et al., "Characterization and chromosomal localization of the human proto–oncogene BMI–1," *Human Molecular Genetics* 2(10):1597–1603, 1993.

Baxendale et al., "A cosmid contig and high resolution restriction map of the megabase region containing the Huntington's disease gene," *Nature Genetics* 4:181–186, 1993.

Bhargava et al., "Differential expression of four members of the POU family of proteins in activated and phorbol 12–myristate 13–acetate–treated Jurkat T cells," *Proc. Natl. Acad. Sci. USA* 90: 10260–10264, 1993.

Chen and Lim, "The *Caenorhabditis elegans* Small GTP–binding Protein RhoA Is Enriched in the Nerve Ring and Sensory Neurons during Larval Development," *The Journal of Biological Chemsitry* 269(51):32394–32404, 1994.

El–Shirbiny, "Prostate Specific Antigen," *Advances in Clinical Chemistry* 31:99–133, 1994.

Fleischmann et al., "Whole–Genome Random Sequencing and Assembly of *Haemophilus influenzae* Rd," *Science* 269:496–512, 1995.

Gerards et al., "Cloning and expression of a human pro(tea)some β–subunit cDNA: a homologue of the yeast PRE4–subunit essential for peptidylglutamyl–peptide hydrolase activity," *FEBS Letters* 346:151–155, 1994.

Grant et al., "The molecular basis for alternative splicing of the CABP1 transcripts in *Dictyostelium discoideum*," *Nucleic Acid Research* 18(18):5457–5463, 1990.

Groffen et al., "Isolation of Human Oncogene Sequences (v–fes Homolog) from a Cosmid Library," *Science* 216:1136–1138, 1982.

Haarer et al., "Identification of MYO4, a second class V myosin gene in yeast," *Journal of Cell Science* 107:1055–1064, 1994.

Habu et al., "Structure and Regulated Expression of Kunitz Chymotrypsin Inhibitor Genes in Winged Bean [*Psophocarpus tetragonolobus* (L.) DC.]," *J. Biochem.* 111:249–258, 1992.

Heller et al., "Analysis of function and expression of the chick GPA recptor (GPARα) suggests multiple roles in neuronal development," *Development* 121:2681–2693, 1995.

Holowachuk, "Isolation and Characterization of a cDNA Clone for the MHC Class II Chain RT1.D$^{\alpha\ \beta}$ of the Diabetic BB Rat," *Immunogenetics* 22:665–671, 1985.

Jacquet et al., "Sequence analysis of a *Dictyostelium discoideum* gene coding for an active diydroorotate dehydrogenase in yeast," *Biochimie* 67(6): 583–588, 1995.

Johnston et al., "Complete Nucleotide Sequence of *Saccharomyces cerevisiae* Chromosome VIII," *Science* 265:2077–2082, 1994.

Jung et al., "Structural Characterization of the Rat Carboxypeptidase–E Gene," *Molecular Endocrinology* 5:1257–1268, 1991.

Matsuda et al., "ATP Synthase γ–Subunit Gene and Tissue–specific Splicing," *J. Biol. Chem.* 268(33):24950–24958, 1993.

McAllister et al., "Molecular cloning of a serotonin receptor from human brain (5HT1E):A fifth 5HT1–like subtype," *Proc. Natl. Acad. Sci. USA* 89:5517–5521, 1992.

Osband and Ross, "Problems in the investigational study and clinical use of cancer immunotherapy," *Immunology Today* 11(6):193–195, 1990.

Rearden, "A New Lim Protein Containing An Autoepitope Homologous To Senescent Cell Antigen", *Biochemical and Biophysical Research Communications* 201(3):1124–1131, 1994.

(List continued on next page.)

*Primary Examiner*—Paula K. Hutzell
*Assistant Examiner*—Minh-Tam Davis
*Attorney, Agent, or Firm*—Seed PLLC

[57] ABSTRACT

Compounds and methods for treating and diagnosing prostate cancer are provided. The inventive compounds include polypeptides containing at least a portion of a prostate protein. Vaccines and pharmaceutical compositions for immunotherapy of prostate cancer comprising such polypeptides or DNA molecules encoding such polypeptides are also provided. The inventive polypeptides may also be used to generate antibodies useful for the diagnosis and monitoring of prostate cancer. Nucleic acid sequences for preparing probes, primers, and polypeptides are also provided.

3 Claims, 3 Drawing Sheets

OTHER PUBLICATIONS

Schuetz et al., "Isolation of a cDNA for HSF2:Evidence for two heat shock factor genes in humans," *Proc. Natl. Acad. Sci. USA* 88:6911–6915, 1991.

Sheldon and Kingston, "Hydrophobic coiled–coil domains regulate the subcellular localization of human heat shock factor 2," *Genes & Development* 7:1549–1558, 1993.

Weissbach et al., "Identification of a Human RasGAP–related Protein Containing Calmodulin–binding Motifs," *J. Biol. Chem.* 269(32):20517–20521, 1994.

Wilson et al., "2.2 Mb of contiguous nucleotide sequence from chromosome III of *C. elegans,*" *Nature* 368:32–38, 1994.

Yasuda et al., "Molecular evidence for a role of domestic ducks in the introduction of avian H3 influenza viruses to pigs in southern China, where the A/Hong Kong/68 (H3N2) strain emerged," *Journal of General Virology* 72(2007–2010), 1991.

COMPOUNDS AND METHODS FOR IMMUNOTHERAPY AND IMMUNODIAGNOSIS OF PROSTATE CANCER

CROSS-REFERENCE TO RELATED APPLICATIONS

This application is a continuation-in-part of U.S. application Ser. No. 08/633,840, filed Apr. 11, 1996, now abandoned which is a continuation-in-part of U.S. application Ser. No. 08/616,745, filed Mar. 15, 1996, now abandoned.

TECHNICAL FIELD

The present invention relates generally to the treatment, diagnosis and monitoring of prostate cancer. The invention is more particularly related to polypeptides comprising at least a portion of a prostate protein. Such polypeptides may be used in vaccines and pharmaceutical compositions for treatment of prostate cancer. The polypeptides may also be used for the production of compounds, such as antibodies, useful for diagnosing and monitoring the progression of prostate cancer, and possibly other tumor types, in a patient.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Three prostate specific proteins—prostate specific antigen (PSA) and prostatic acid phosphatase (PAP)—have limited diagnostic and therapeutic potential. PSA levels do not always correlate well with the presence of prostate cancer, being positive in a percentage of non-prostate cancer cases, including benign prostatic hyperplasia (BPH). furthermore, PSA measurements correlate with prostate volume, and do not indicate the level of metastasis.

Accordingly, there remains a need in the art for improved vaccines and diagnostic methods for prostrate cancer.

SUMMARY OF THE INVENTION

The present invention provides compounds and methods for immunotherapy and diagnosis of prostate cancer. In one aspect, polypeptides are provided comprising at least an immunogenic portion of a prostate protein having a partial sequence as provided in SEQ ID NOS: 2 and 4–8, or a variant of such a protein that differs only in conservative substitutions and/or modifications, together with polypeptides comprising an immunogenic portion of a prostate protein, or a variant thereof, wherein the protein comprises an amino acid sequence encoded by a DNA sequence selected from the group consisting of sequences recited in SEQ ID NOS: 11, 13–19, 58 and 59, the complements of said sequences, and DNA sequences that hybridize to a sequence recited in SEQ ID NOS: 11, 13–19, 58 and 59, or a complement thereof under moderately stringent conditions.

In related aspects, DNA molecules encoding the above polypeptides, expression vectors comprising such DNA molecules and host cells transformed or transfected with such expression vectors are also provided. In preferred embodiments, the host cells are selected from the group consisting of E. coli, yeast and mammalian cells.

The present invention also provides pharmaceutical compositions comprising one or more of the polypeptides of SEQ ID NOS: 1–8, 20, 21, 25–31, 44–57, 60 or 61, or DNA molecules of SEQ ID NOS: 9–19, 22–24, 32–43, 58 or 59 and a physiologically acceptable carrier. The invention further provides vaccines comprising one or more of such polypeptides or DNA molecules in combination with a non-specific immune response enhancer.

In yet another aspect, methods are provided for inhibiting the development of prostate cancer in a patient, comprising administering an effective amount of one or more of the polypeptides of SEQ ID NOS: 1–8, 20, 21, 25–31, 44–57, 60 or 61, or DNA molecules of SEQ ID NOS: 9–19, 22–24, 32–43, 58 or 59 to a patient in need thereof.

In further aspects, methods are provided for detecting prostate cancer in a patient, comprising: (a) contacting a biological sample obtained from a patient with a binding agent that is capable of binding to a polypeptide of SEQ ID NOS: 1–8, 20, 21, 25–31, 44–57, 60 or 61; and (b) detecting in the sample a protein or polypeptide that binds to the binding agent.

In related aspects, methods are provided for monitoring the progression of prostate cancer in a patient, comprising: (a) contacting a biological sample obtained from a patient with a binding agent that is capable of binding to a polypeptide of SEQ ID NOS: 1–8, 20, 21, 25–31, 44–57, 60 or 61; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the polypeptides described above, as well as diagnostic kits comprising such antibodies, and methods of using such antibodies to inhibit the development of prostate cancer.

The present invention also provides methods for detecting prostate cancer comprising: (a) obtaining a biological sample from a patient; (b) contacting the sample with at least two oligonucleotide primers in a polymerase chain reaction, at least one of the oligonucleotide primers being specific for a DNA sequence selected from the group consisting of SEQ ID NOS: 9–19, 22–24, 32–43, 58 and 59; and (c) detecting in the sample a DNA sequence that amplifies in the presence of the oligonucleotide primer. In one embodiment, the oligonucleotide primer comprises at least about 10 contiguous nucleotides of a DNA sequence selected from the group consisting of SEQ ID NOS: 9–19, 22–24, 32–43, 58 and 59.

In a further aspect, the present invention provides a method for detecting prostate cancer in a patient comprising: (a) obtaining a biological sample from the patient; (b) contacting the sample with an oligonucleotide probe specific for a DNA sequence selected from the group consisting of SEQ ID NOS: 9–19, 22–24, 32–43, 58 and 59; and (c) detecting in the sample a DNA sequence that hybridizes to the oligonucleotide probe. In one embodiment, the oligonucleotide probe comprises at least about 15 contiguous nucleotides of a DNA sequence selected from the group consisting of SEQ ID NOS: 9–19, 22–24, 32–43, 58 and 59.

These and other aspects of the present invention will become apparent upon reference to the following detailed

DETAILED DESCRIPTION OF THE INVENTION

Figure 1:
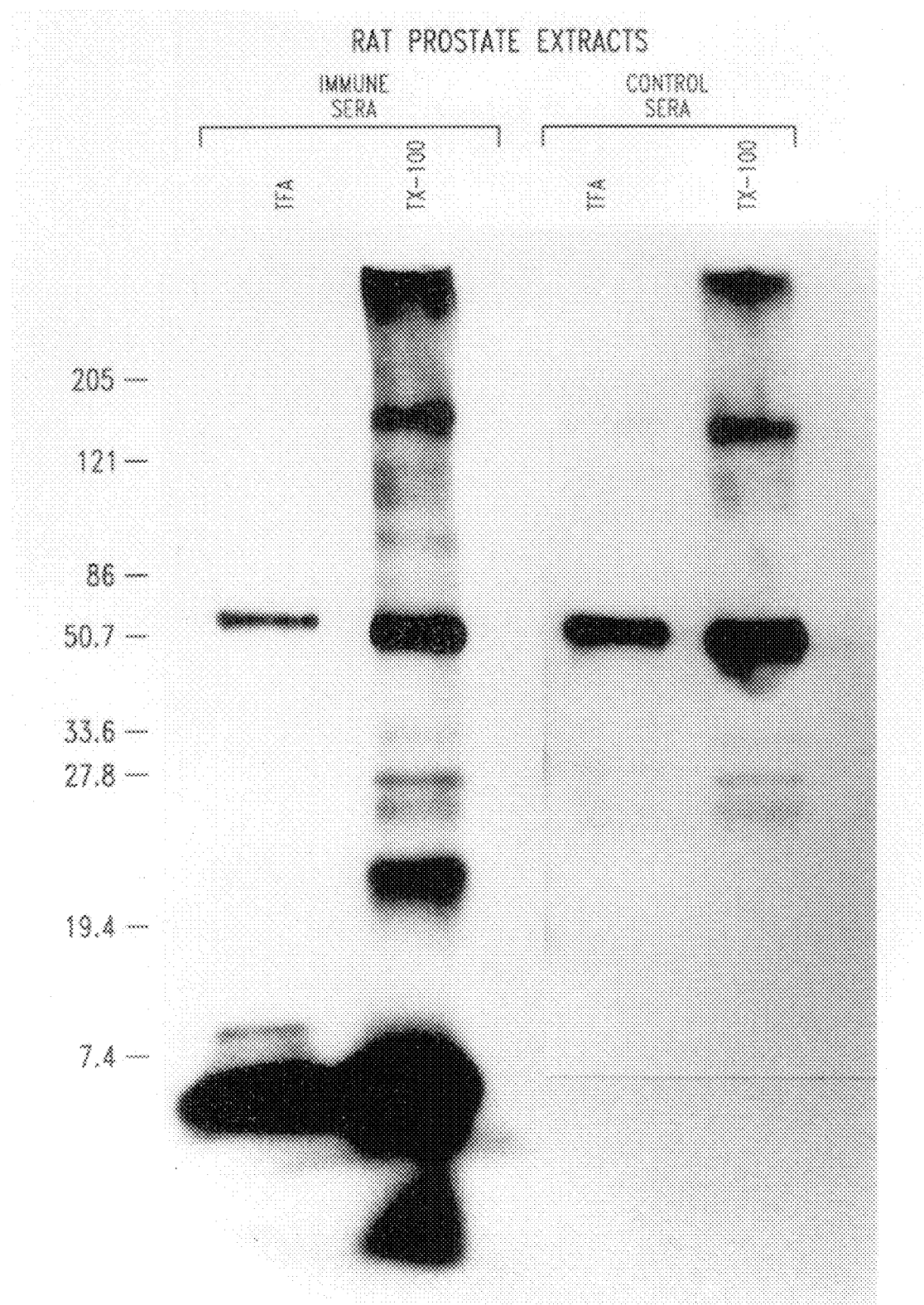
FIG. 1 illustrates a Western blot analysis of sera obtained form rats immunized with rate prostate extract.

As noted above, the present invention is generally directed to compositions and methods for the immunotherapy, diagnosis and monitoring of prostate cancer. The inventive compositions are generally polypeptides that comprise at least a portion of a human prostate protein, the protein demonstrating immunoreactivity with human prostate sera. Also included within the present invention are molecules (such as an antibody or fragment thereof) that bind to the inventive polypeptides. Such molecules are referred to herein as "binding agents."

In particular, the subject invention discloses polypeptides comprising at least a portion of a human prostate protein provided in SEQ ID NOS: 2 and 4–8, or a variant of such a protein that differs only in conservative substitutions and/or modifications. As used herein, the term "polypeptide" encompasses amino acid chains of any length, including full length proteins, wherein the amino acid residues are linked by covalent peptide bonds. Thus, a polypeptide comprising a portion of one of the above prostate proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human prostate protein is a portion that reacts either with sera derived from an individual inflicted with autoimmune prostatitis or with sera derived from a rat model of autoimmune prostatitis. In other words, an immunogenic portion is capable of eliciting an immune response and as such binds to antibodies present within prostatitis sera. Autoimmune prostatitis may occur, for example, following treatment of bladder cancer by administration of Bacillus Calmette-Guerin (BCG), an avirulent strain of *Mycobacterium bovis*. In the rat model of autoimmune prostatitis, rats are immunized with a detergent extract of rat prostate. Sera from either of these sources may be used to react with the human prostate derived polypeptides described herein. Antibody binding assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A.

A "variant," as used herein, is a polypeptide that differs from the recited polypeptide only in conservative substitutions and/or modifications, such that the immunotherapeutic, antigenic and/or diagnostic properties of the polypeptide or molecules that bind to the polypeptide, are retained. For prostate proteins with immunoreactive properties, variants may generally be identified by modifying one of the above polypeptide sequences, and evaluating the immunoreactivity of the modified polypeptide. For prostate proteins useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides having one of the sequences provided in SEQ ID NOS: 1 to 8, 20, 21 and 25–31 may be isolated from a suitable human prostate adenocarcinoma cell line, such as LnCap.fgc (ATCC No. 1740-CRL). LnCap.fgc is a prostate adenocarcinoma cell line that is a particularly good representation of human prostate cancer. Like the human cancer, LnCap.fgc cells form progressively growing tumors as xenografts in SCID mice, respond to testosterone, secrete PSA and respond to the presence of bone marrow components (e.g., transferrin). In particular, the polypeptides may be isolated by expression screening of a LnCap.fgc cDNA library with human prostatitis sera using techniques described, for example, in Sambrook et al., *Molecular Cloning: A Laboratory Manual*, Cold Spring Harbor Laboratories, Cold Spring Harbor, N.Y. (and references cited therein), and as described in detail below. The polypeptides of SEQ ID NOS: 48 and 49 may be isolated from the LnCap/fgc cell line by screening with sera from the rat model of autoimmune prostatitis discussed above. The polypeptides of SEQ ID NOS: 50–56 may be isolated from the LnCap/fgc cell line by screening with human prostatitis sera as described in detail in Example 4. The polypeptides of SEQ ID NOS: 44–47 may be isolated from human seminal fluid as described in detail in Example 2. The polypeptides of SEQ ID NOS: 60 and 61 may be isolated by screenign a prostate tumor cDNA expression library with monkey antiprostate sera as detailed below in Example 6. Once a DNA sequence encoding a polypeptide is obtained, any of the above modifications may be readily introduced using standard mutagenesis techniques, such as oligonucleotide-directed site-specific mutagenesis.

The polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

Polypeptides of the present invention that comprise an immunogenic portion of a prostate protein may generally be used for immunotherapy of prostate cancer, wherein the polypeptide stimulates the patient's own immune response to prostate tumor cells. In further aspects, the present invention provides methods for using one or more of the immunoreactive polypeptides of SEQ ID NOS: 1 to 8, 20, 21, 25–31, 44–57, 60 and 61 (or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides may be used to treat prostate cancer or to inhibit the development of prostate cancer. The polypeptides may be administered either prior to or following surgical removal of primary tumors and/or treatment by administration of radiotherapy and conventional chemotherapeutic drugs.

In these aspects, the polypeptide is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such as an adjuvant, biodegradable microsphere (e.g., polylactic galactide) or a liposome (into which the polypeptide is incorporated). Pharmaceutical compositions and vaccines may also contain other epitopes of prostate cell antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No.4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human prostate tumors.

Binding agents of the present invention may generally be prepared using methods known to those of ordinary skill in the art, including the representative procedures described herein. Binding agents are capable of differentiating between patients with and without prostate cancer, using the representative assays described herein. In other words, antibodies or other binding agents raised against a prostate protein, or a suitable portion thereof, will generate a signal indicating the presence of primary or metastatic prostate cancer in at least about 20% of patients afflicted with the disease, and will generate a signal indicating the absence of the disease in at least about 90% of individuals without primary or metastatic prostate cancer. Suitable portions of such prostate proteins are portions that are able to generate a binding agent that indicates the presence of primary or metastatic prostate cancer in substantially all (i.e., at least about 80%, and preferably at least about 90%) of the patients for which prostate cancer would be indicated using the full length protein, and that indicate the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

The ability of a polypeptide prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 20% of primary or metastatic prostate tumors by such procedures are considered to be able to generate antibodies capable of detecting primary or metastatic human prostate tumors. Polypeptide specific antibodies may be used alone or in combination to improve sensitivity.

Polypeptides capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include blood, sera, urine and/or prostate secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate prostate tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g. via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise does of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify prostate tumor-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80% identity, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect prostate and/or prostate tumor sequences in biological samples, preferably blood, semen or prostate and/or prostate tumor tissue.

The following Examples are offered by way of illustration and not by way of limitation.

EXAMPLES

Example 1

A. Isolation of Polypeptides from LnCap.fgc Using Human Prostatitis Sera

Representative polypeptides of the present invention were isolated by screening a human prostate cancer cell line with human prostatitis sera as follows. A human prostate adenocarcinoma cDNA expression library was constructed by reverse transcriptase synthesis from mRNA purified from the human prostate adenocarcinoma cell line LnCap.fgc (ATCC No. 1740-CRL), followed by insertion of the resulting cDNA clones in Lambda ZAP II (Stratagene, La Jolla, Calif.).

Human prostatitis serum was obtained from a patient diagnosed with autoimmune prostatitis following treatment of bladder carcinoma by administration of BCG. This serum was used to screen the LnCap cDNA library as described in Sambrook et al., *Molecular Cloning: A Laboratory Manual*, Cold Spring Harbor Laboratories, Cold Spring Harbor, N.Y., 1989. Specifically, LB plates were overlaid with approximately $10^4$ pfu of the LnCap cDNA library and incubated at 42° C. for 4 hours prior to obtaining a first plaque lift on isopropylthio-beta-galactoside (IPTG) impregnated nitrocellulose filters. The plates were then incubated for an additional 5 hours at 42° C. and a second plaque lift was prepared by incubation overnight at 37° C. The filters were washed three times with PBS-T, blocked for 1 hours with PBS (containing 1% Tween 20™) and again washed three times with PBS-T, prior to incubation with human prostatitis sera at a dilution of 1:200 with agitation overnight. The filters were then washed three times with PBS-T and incubated with $^{125}$I-labeled Protein A (1 µl/15 ml PBS-T) for 1 hour with agitation. Filters were exposed to film for variable times, ranging from 16 hours to 7 days. Plaques giving signals on duplicate lifts were re-plated on LB plates. Resulting plaques were lifted with duplicate filters and these filters were treated as above. The filters were incubated with human prostatitis sera (1:200 dilution) at 4° C. with agitation overnight. Positive plaques were visualized with $^{125}$I-Protein A as described above with the filters being exposed to film for variable times, ranging from 16 hours to 11 days. In vivo excision of positive human prostatitis antigen cDNA clones was performed according to the manufacturer's protocol.

B. Characterization of Polypeptides

DNA sequence for positive clones was obtained using forward and reverse primers on an Perkin Elmer/Applied Biosystems Division Automated Sequencer Model 373A (Foster City, Calif.). The cDNA sequences encoding the isolated polypeptides, hereinafter referred to as HPA8, HPA13, HPA15–HPA17, HPA20, HPA25, HPA28, HPA29, HPA32–HPA38 and HPA41 are presented in SEQ ID NOS: 32 and 33, 34 and 35, 36, 9 and 10, 11, 12, 13 and 14, 15, 37 and38, 16, 39, 22 and 23, 17 and 18, 19, 24, 40 and 41, 42 and 43, respectively. The 3' sequences of HPA16 and HPA20 are identical. HPA13, HPA16, HPA20, HPA29 and HPA33 are believed to be overlapping clones with novel 5' end points. Two of the positive clones were determined to be identical to HPA15. Also, HPA15, HPA34 and HPA37 were found to be overlapping clones. The expected N-terminal amino acid sequences of the isolated polypeptides HPA16, HPA17, HPA20, HPA25, HPA28, HPA32, HPA35, HPA36, HPA34, HPA37, HPA8, HPA13, HPA15, HPA29, HPA33, HPA38 and HPA41, based on the determined cDNA sequences in frame with the N-terminal portion of β-galactosidase (lacZ) are presented in SEQ ID NOS: 1–8, 20, 21 and 25–31, respectively.

The determined cDNA and expected amino acid sequences for the isolated polypeptides were compared to known sequences in the gene bank using the EMBL and GenBank (Release 91) databases, and also the DNA STAR system. The DNA STAR system is a combination of the Swiss, PIR databases along with translated protein sequences (Release 91). No significant homologies to HPA17, HPA25, HPA28, HPA32, HPA35 and HPA36 were found.

The determined cDNA sequence for HPA8 was found to have approximately 100% identity with the human proto-oncogene BMI-1 (Alkema, M. J. et al., *Hum. Mol. Gen.* 2:1597–1603, 1993). Search of the DNA database with 5' and 3' cDNA sequence encoding HPA 13 revealed 100% identity with a known cDNA sequence from a human immature myeloid cell line (GenBank Acc. No. D63880). Search of the protein database with the deduced amino acid sequence for HPA13 revealed 100% identity with the open reading frame encoded by the same human cDNA sequence. Search of the protein database with the expected amino acid sequence for HPA15, revealed high homology (60% identity) with a *Saccharomyces cerevisiae* predicted open reading frame (Swiss/PIR Acc. No. S46677), and 100% identity with a human protein from pituitary gland modulating intestinal fluid secretion (Lonnroth, I., *J. Biol. Chem.* 35:20615–20620, 1995). The deduced amino acid sequence for HPA38 was found to have 100% identity with human heat shock factor protein 2 (Schuetz, T. J. et al., *Proc. Natl. Acad. Sci. USA* 88:6911–6915, 1991). Search of the DNA database with the 5' DNA sequence for HPA41 and search of the protein database with the deduced amino acid sequence revealed 100% identity with a human LIM protein (Rearden, A., *Biochem. Biophys. Res. Commun.* 201:1124–1131, 1994). To the best of the inventors' knowledge, except for LIM protein, none of the inventive polypeptides have been previously shown to be present in human prostate.

Positive phagemid viral particles were used to infect *E. coli* XL-1 Blue MRF', as described in Sambrook et al., supra. Induction of recombinant protein was accomplished by the addition of IPTG. Induced and uninduced lysates were run in duplicate on SDS-PAGE and transferred to nitrocellulose filters. Filters were reacted with human prostatitis sera (1:200 dilution) and a rabbit sera (1:200 or 1:250 dilution) reactive with the N-terminal 4 Kd portion of lacZ. Sera incubations were performed for 2 hours at room temperature. Bound antibody was detected by addition of $^{125}$I-labeled Protein A and subsequent exposure to film for variable times ranging from 16 hours to 11 days. The results of the immunoblots are summarized in Table I, wherein (+) indicates a positive reaction and (−) indicates no reaction.

TABLE I

| Antigen | Human Prostatitis Sera | Anti-lacZ Sera | Protein Mass/Kd |
|---|---|---|---|
| HPA8 | (−) | (−) | |
| HPA13 | (+) | (+) | |
| HPA15 | (+) | (+) | 50 |
| HPA16 | (+) | (+) | 40 |
| HPA17 | (+) | (−) | 40 |
| HPA20 | (+) | (+) | 38 |
| HPA25 | (−) | (+) | 32 |
| HPA28 | (−) | (−) | |
| HPA29 | (+) | (+) | |
| HPA32 | (−) | (−) | |
| HPA33 | (+) | (+) | |
| HPA34 | not tested | (+) | 50 |
| HPA35 | (−) | (−) | |
| HPA36 | (−) | (−) | |
| HPA37 | not tested | (+) | 50 |
| HPA38 | (−) | (−) | |
| HPA41 | not tested | (+) | |

Positive reaction of the recombinant human prostatitis antigens with both the human prostatitis sera and anti-lacZ sera indicate that reactivity of the human prostatitis sera is directed towards the fusion protein. Cloned antigens showing reactivity to the human prostatitis sera but not to anti-lacZ sera indicate that the reactive protein is likely initiating within the clone. Antigens reactive with the anti-lacZ sera but not with the human prostatitis sera may be the result of the human prostatitis sera recognizing conformational epitopes, or the antigen-antibody binding kinetics may be such that the 2 hour sera exposure in the immunoblot is not sufficient. Antigens not reactive with either sera are not being expressed in *E. coli*, and reactive epitopes may be within the fusion protein or within an internal open reading frame. Due to the instability of recombinant antigens from HPA13, HPA29 and HPA33, it was not possible to determine the size of the recombinant antigens.

The expression of representative human prostatitis antigens was investigated by RT-PCR in four different human cell lines (including two metastatic prostate tumor lines LNCaP and DU145), normal prostate, breast, colon, kidney, stomach, lung and skeletal muscle tissue, nine different prostate tumor samples and three different breast tumor samples. The results of these studies are shown in Table II.

TABLE II

Analysis of HPA clone mRNA expression by RT-PCR in human cell lines, normal tissues and tumors

| Clone | LNCaP | DU145 | MCF-12A | HBL-100 | Prostate | Breast | Colon | Kidney | Stomach | Lung | Skel. Muscle |
|---|---|---|---|---|---|---|---|---|---|---|---|
| hpa-17 | + | ++ | + | + | + | − | ± | − | − | + | + |
| hpa-20 | +++ | ++++ | NT | NT | ± | NT | NT | − | NT | + | NT |
| hpa-28 | + | +++ | + | + | + | − | ± | + | − | + | ± |

| | Prostate Tumors (n = 9) | | | | | | | | | Breast Tumors (n = 3) | | |
|---|---|---|---|---|---|---|---|---|---|---|---|---|
| Clone | Tumor 1 | Tumor 2 | Tumor 3 | Tumor 4 | Tumor 5 | Tumor 6 | Tumor 7 | Tumor 8 | Tumor 9 | Tumor 1 | Tumor 2 | Tumor 3 |
| hpa-17 | + | + | + | − | + | + | ± | − | − | + | ++ | ++ |
| hpa-20 | + | + | NT | NT | NT | NT | NT | NT | NT | + | + | +++ |
| hpa-28 | + | + | ± | − | + | + | ++ | ± | − | ++ | +++ | + | mRNA expression of representative antigens in LNCaP and normal prostate, kidney, liver, stomach, lung and pancreas was also investigated by RNase protection. The results of these studies are provided in Table III.

TABLE III

Analysis of HPA clone mRNA expression by RNase protection in LNCaP and normal human tissues

| Clone | LNCaP | Prostate | Kidney | Liver | Stomach | Lung | Pancreas |
|---|---|---|---|---|---|---|---|
| hpa-15 | + | − | ++ | ++ | + | − | ++ |
| hpa-20 | +++++ | + | + | + | + | NT | NT |
| hpa-25 | + | + | + | + | ++ | ++ | NT |
| hpa-32 | NT | ++ | + | + | NT | ++ | NT |
| hpa-35 | +++ | +++ | NT | + | + | +++ | + |
| hpa-36 | + | + | NT | NT | + | + | + |

Example 2

A. Isolation and Characterization of Rat Steroid Binding Protein

Immune sera was obtained from rats immunized with rat prostate extract to generate antibodies to self prostate antigens. Specifically, rats were prebled to obtain control sera prior to being immunized with a detergent extract of rat prostate (in PBS containing 0.1% Triton) in Freunds complete adjuvant. A boost of incomplete Freunds adjuvant was given 3 weeks after the initial immunization and sera was harvested at 6 weeks.

Figure 2:
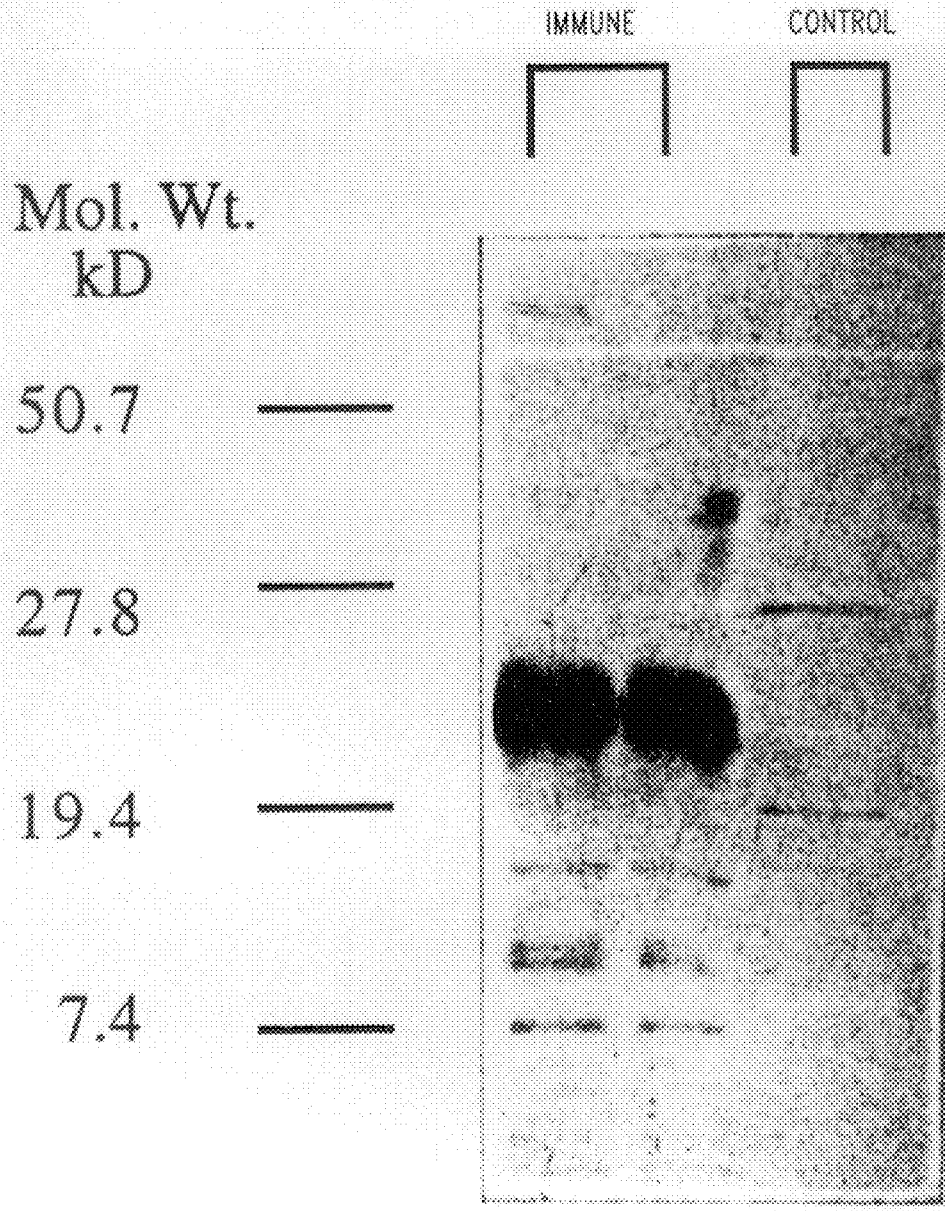
FIG. 2 illustrates a non-reduced SDS PAGE of the rat immunizing preparation of FIG. 1.

The sera thus obtained was subjected to ECL Western blot analysis (Amersham International, Arlington Heights, Ill.) using the manufacturer's protocol and a rat prostate protein was identified, as shown in FIG. 1. After reduction, SDS-PAGE revealed a broad silver staining band migrating at 7 kD. Without reduction, a strong band was seen at 24 kD (FIG. 2). This protein was purified by ion exchange chromatography and subjected to gel electrophoresis under reduced conditions. Three bands were seen, indicating the presence of three chains within the protein: a 6–8 kD chain (C1), a 8–10 kD chain (C2) and a 10–12 kD chain (C3). The protein was further purified by reverse phase HPLC on a Delta™ C18 300 A° 5 μm column, column size 3.9×300 mm (Waters-Millipore, Milford, Mass.). The sample containing 100 μg of protein was dissolved in 0.1% trifluoroacetic acid (TFA), pH 1.9 and polypeptides were eluted with a linear gradient of acetonitrile (0–60%) in 0.1% TFA pH 1.9 at a flow rate of 0.5 mL/min for 1 hour. The eluent was monitored at 214 nm. Two peaks were obtained, a C1–C3 dimer and a C2–C3 dimer. The amino terminus of the C2 chain was found to be blocked. The C1 and C3 chains were sequenced on a Perkin Elmer/Applied Biosystems Inc. Procise Model 494 protein sequencer and found to have the following amino terminal sequences (SEQ ID NOS: 44 and 45, respectively).

(a) Ser-Gln-Ile-Cys-Glu-Leu-Val-Ala-His-Glu-Thr-Ile-Ser-Phe-Leu; and (b) Xaa-Xaa-Xaa-Xaa-Xaa-Ser-Ile-Leu-asp-Glu-Val-Ile-Arg-Gly-Thr, wherein Xaa may be any amino acid.

These sequences were compared to known sequences in the gene bank using the databases discussed in Example 1 and were found to be identical to rat steroid binding protein, also known as estramustine-binding protein (EMBP) (Forsgren, B. et al., Prog. Clin. Biol. Res. 75A:391–407, 1981; Forsgren, B. et al., Proc. Natl. Acad. Sci. USA 76:3149–53, 1979). This protein is a major secreted protein in rat seminal fluid and has been shown to bind steroid, cholesterol and proline rich proteins. EMBP has been shown to bind estramustine and estromustine, the active metabolites of estramustine phosphate. Estramustine phosphate has been found to be clinically useful in treating advanced prostate cancer in patients who do not respond to standard hormone ablation therapy (see, for example, Van Poppel, H. et al., Prog. Clin. Biol. Res. 370:323–41, 1991).

B. Isolation of Putative Human Homologue to Rat Steroid Binding Protein

Purified rat steroid binding protein was obtained from freshly excised rat prostate and used to subcutaneously immunize a New Zealand white virgin female rabbit (150 μg purified rat steroid binding protein in 1 ml of PBS and 1 ml of incomplete Freund's adjuvant containing 100 μg of muramyl dipeptide (adjuvant peptide, Calbiochem, La Jolla, Calif.). Six weeks later the rabbit was boosted subcutaneously with the same protein dose in incomplete Freund's adjuvant. Finally, the rabbit was boosted intravenously two weeks later with 100 μg protein in PBS and the sera harvested two weeks after the final immunization.

The resulting rabbit antisera was used to screen the LnCap.fgc cell line without success. The rabbit antisera was subsequently used to screen human seminal fluid anion exchange chromatography pools using the protocol detailed below in Example 3. This analysis indicated an approximately 18–22 kD cross-reactive protein. The seminal fluid fraction of interest (Fraction 1) was separated into individual components by SDS-PAGE under non-reducing conditions, blotted onto a PVDF membrane, excised and digested with CNBr in 70% formic acid. The resulting CNBr fragments were resolved on a tricine gel system, again electroblotted to PVDF and excised. The sequence for one peptide was determined as follows:

Val-Val-Lys-Thr-Tyr-Leu-Ile-Ser-Ser-Ile-Pro-Leu-Gln-Gly-Ala-Phe-Asn-Tyr-Lys-Tyr-Thr-Ala (SEQ ID NO: 46).

This sequence was compared to known sequences in the gene bank using the databases identified above and was unexpectedly found to be identical to gross cystic disease fluid protein, a protein whose expression was previously found to correlate with the presence of metastatic breast cancer (Murphy, L. C. et al., *J. Biol. Chem.* 262:15236–15241, 1987). To the best of the inventors' knowledge, this protein has not been previously identified in male tissues.

The ability of Fraction 1 as described above, to bind to steroid was investigated as follows. Purified rat steroid binding protein (RSBP) and fraction 1 were subjected to SDS-PAGE and transferred onto nitrocellulose filters. Specifically, 1.5 μg of RSBP/gel lane and 4 μg of fraction 1/gel lane were electrophoresed in parallel on a 4–20% gradient Laemmli gel (BioRad), then electrophoretically transferred to nitrocellulose. After protein transfer, the nitrocellulose was blocked for 1 hour at room temperature in 1% Tween 20 in PBS, rinsed three times for 10 min each in 10 ml 0.1% Tween 20 in PBS plus 0.5 M NaCl, then probed with either 1) 0.87 μM progesterone conjugated to horseradish peroxidase (HRP, Sigma) diluted in the rinse buffer; 2) 0.87 μM progesterone HRP with 200 μM estramustine; or 3) 0.87 μM progesterone HRP plus 400 μM unlabelled progesterone and 200 μM estramustine. Each reaction mixture was incubated for 1 hour at room temperature and washed three times for 10 min each with 0.1% Tween 20, PBS, and 0.5 M NaCl. The blots were then developed (ECL system, Amersham) to reveal progesterone HRP binding proteins that are also capable of binding estramustine.

Figures 3A, 3B:
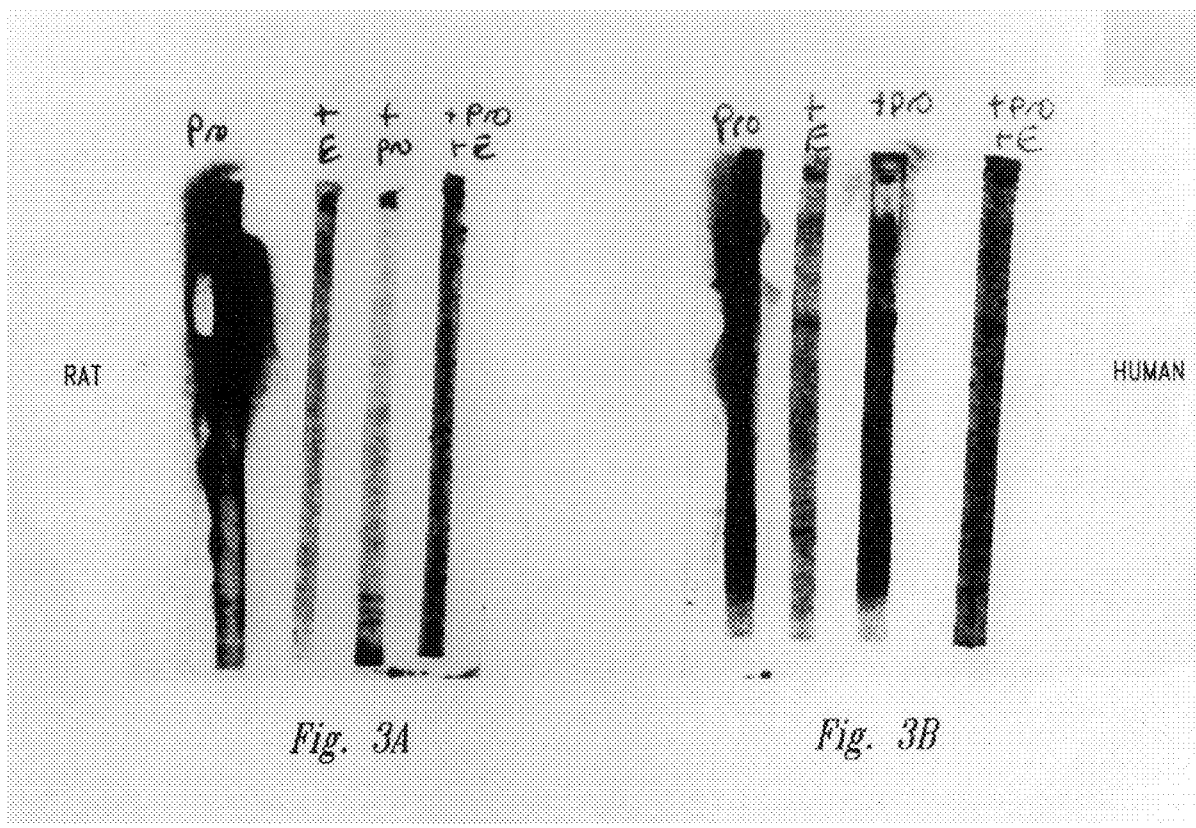
FIG. 3 illustrates the binding of a putative human homologue of rat steroid binding protein to progesterone and to estramustine.

With both rat steroid binding protein and Fraction 1, three bands were obtained that bound HRP-progesterone and that were competed out with unlabelled progesterone and estramustine (FIG. 3). These results indicate that the three bands isolated from human seminal fluid as described above bind hormone and correspond in number of polypeptides to the chains C1, C2 and C3 of rat steroid binding protein, although slightly bigger in size, either due to primary sequence or secondary post-translational modifications.

This putative homologue of rat steroid binding protein was also identified in a subsequent screen of human seminal fluid using the rabbit antisera detailed above. Specifically a hydrophobic 22 kD/65 kD aggregate protein was obtained which, following CNBr digestion of the 22 kD band, provided a peptide having the following sequence:

Val-Val-Lys-Thr-Tyr-Leu-Ile-Ser-Ser-Ile-Pro-Leu-Gln-Ala-Phe-Asn-Tyr-Lys-Tyr-Thr-Ala (SEQ ID NO: 47).

This peptide was found to correspond to residues 67 through 87 of gross cystic disease fluid protein and was identified again utilizing human autoimmune prostatitis sera as discussed below in Example 4.

Example 3

Isolation and Characterization of Polypeptides Isolated from LnCaP.fgc Using Rat Prostatitis Sera A LnCap.fgc cell pellet was homogenized (10 gm cell pellet in 10 ml) by resuspension in PBS, 1% NP-40 and 60 μg/ml phenylmethylsulfonyl fluoride (PMSF) (Sigma, St. Louis, Mo.) then 10 strokes in a Dounce homogenizer. This was followed by a 30 second probe sonication and another 10 strokes in the Dounce homogenizer. The resulting slurry was centrifuged at 10,000×G, and the supernatant filtered with a 0.45 μM filter (Amicon, Beverly, Mass.) then applied to a BioRad (Hercules, Calif.) Macro-Prep Q-20 anion exchange resin. Proteins were eluted with a 70 minute 0 to 0.8 M NaCl gradient in 20 mM tris pH 7.5 at a flow rate of 8 ml/min. Fractions were cooled, concentrated with 10 kD MWCO centriprep concentrators (Amicon) and stored at −20° C. in the presence of 60 μg/ml PMSF. The ion exchange pools were then examined by electrophoresis on 4–20% tris glycine Ready-Gels (BioRad) and subsequent transfer to nitrocellulose filters. Ion exchange pools of interest were identified by ECL (Amersham International) Western analysis, using the rat sera described above in Example 2A. This analysis indicated an approximately 65 kD protein eluting at 0.08 to 0.13 M NaCl. The rat sera reactive ion exchange pool was subjected to HPLC and subsequent Western analysis to identify the protein fraction of interest. This protein was then digested for 24 hours at 25° C. in 70% formic acid saturated with CNBr to cleave at methionine residues.

The resulting CNBr fragments were purified by microbore HPLC using a Vydac C18 column (Hesperia, Calif.), column size 1×150 mM in a Perkin Elmer/Applied Biosystems Inc. (Foster City, Calif.) Division Model 172 HPLC. Fractions were eluted from the column with a gradient of 0 to 60% of acetonitrile at a flow rate of 40 μl per minute. The eluent was monitored at 214 nm. The resulting fractions were loaded directly onto a Perkin Elmer/Applied Biosystems Inc. Procise 494 protein sequencer and sequenced using standard Edman chemistry from the amino terminal end. Two different peptides having the following sequences were obtained:

(a) Xaa-Ala-Lys-Lys-Phe-Leu-Asp-Ala-Glu-His-Lys-Leu-Asn-Phe-Ala (SEQ ID NO: 48); and (b) Xaa-Xaa-Xaa-Lys-Ile-Lys-Lys-Phe-Ile-Gln-Glu-Asn-Ile-Phe-Gly, wherein Xaa may be any amino acid (SEQ ID NO: 49).

These sequences were compared to known sequences in the gene bank using databases identified above, and identified as residues 286 through 300 and 228 through 242, respectively, of probable protein disulfide isomerase ER-60 precursor, hereinafter referred to as ER-60 (Bado, R. J. et al., *Endocrinology* 123:1264–1273, 1988). This antigen is also known as phospholipase C-alpha (see PCT WO 95/08624). Residues 285 and 227 of ER-60 are methionines, consistent with the above sequences being cyanogen bromide fractions.

ER-60 is a resident endoplasmic protein with multiple biological activities, including disulfide isomerase and restricted cysteine protease activity. In particular, ER-60 has been shown to preferentially degrade calnexin, a protein involved in presentation of antigens via the Class I major histocompatability complex, or MHC, pathway. ER-60 and a related family member, ER-72, have been shown to be over-expressed in colon cancer, with truncated forms of ER-60 exhibiting increased enzymatic activity (Egea, G. et al., *J. Cell. Sci.* (*England*) 105:819–30, 1993). However, to the best of the inventors' knowledge, this polypeptide has not been previously shown to be present or overexpressed in human prostate. Recently, ER-60 gene expression has been correlated with induction of contact inhibition of cell proliferation (Greene, J. J. et al., *Cell. Mol. Biol.* 41:473–80, 1995). Thus, if ER-60 is also truncated and non-functional in prostate cancer, as it is in colon cancer, the resultant loss of contact inhibition would lead to neoplastic transformation and tumor progression.

Example 4

Isolation and Characterization of Polypeptides Isolated from LnCaP.fgc Using Human Prostatitis Sera The human prostatitis sera described above in Example 1 was used to screen the LnCaP.fgc cell line using the ion exchange techniques described above in Example 3. Reactive ion exchange pools were purified by reverse phase HPLC as described previously and the polypeptides shown in SEQ ID NOS: 50–56 were isolated utilizing cross-reactivity with said antisera as the selection criteria. Comparison of these sequences with known sequences in the gene bank using the databases described above revealed the homologies shown in Table II. However, none of these polypeptides have been previously associated with human prostate.

TABLE IV

| SEQ ID NO: | Database Search Identification |
| --- | --- |
| 50 | glyceraldehyde-3-phosphate-dehydrogenase |
| 51 | alpha-human fructose biphosphate aldolase |
| 52 | calreticulin |
| 53 | calreticulin |
| 54 | malate dehydrogenase |
| 55 | cystic disease fluid protein |
| 56 | cystic disease fluid protein |

Example 5

Isolation and Characterization of Polypeptides from Human Seminal Fluid

Polypeptides from human seminal fluid were purified to homogeneity by anion exchange chromatography. Specifically, seminal fluid samples were diluted 1 to 10 with 0.1 mM Bis-Tris propane buffer pH 7 prior to loading on the column. The polypeptides were fractionated into pools utilizing gel profusion chromatography on a Poros (Persepctive Biosystems) 146 II Q/M anion exchange column 4.6 mm×100 mm equilibrated in 0.01 mM Bis-Tris propane buffer pH 7.5. Proteins were eluted with a linear 0–0.5 M NaCl gradient in the above buffer. The column eluent was monitored at a wavelength of 220 nm. Individual fractions were further purified by reverse phase HLPC on a Vydac (Hesperia, Calif.) C18 column.

The resulting fractions were sequenced as described above in Example 3. A peptide having the following N-terminal sequence was obtained:

(c) Met-Asp-Ile-Pro-Gln-Thr-Lys-Gln-Asp-Leu-Glu-Leu-Pro-Lys-Leu (SEQ ID NO:57).

Comparison of this sequence with those of known sequences in the gene bank as described above revealed 100% identity with human placental protein 14 (PP14).

Example 6

Isolation of Polypeptides from a Prostate Tumor cDNA Library using Monkey Anti-Prostate Sera A female cynomologous monkey was immunized with homogenized monkey prostate plus complete Freund's adjuvant. A booster immunization, using the same immunogen, was given one month later. Sera was taken from this monkey two months after the first immunization. This sera was pre-cleared of *E. coli* and phage antigens and used at a 1:200 dilution to screen a primary prostate tumor expression library prepared in Lambda ZAP II (Stratagene).

Two positive clones identified in the screen (hereinafter referred to as JF3 and JF5) were found to be non-sister clones from the same gene. The clones were excised and insert size was determined by restriction digest (JF3=1500 bp, JF5=1000 bp). Complete DNA sequencing of these clones with both vector and internal primers indicated that the sequence of JF5 was found within that of JF3. Similarly, the partial open reading frame found in JF5 was found to be contained wholly within JF3. The determined cDNA sequences for JF3 and JF5 are provided in SEQ ID NO: 58 and 59, respectively, with the corresponding predicted amino acid sequences being provided in SEQ ID NO: 60 and 61, respectively. Comparison of these sequences with those in the gene bank as described above revealed no significant homologies.

The expression of these antigens in various tissue types was investigated using RT-PCR. Over-expression was found in 2 out of 5 prostate tumor samples, 3 out of 5 normal prostate samples, 1 out of 2 breast tumor samples, and in a normal kidney sample and a normal brain sample. Northern analysis indicated that these antigens may be expressed both in prostate and testis.

Example 7

Synthesis of Polypeptides

Polypeptides may be synthesized on an Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyo philized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

We claim:

1. A composition for eliciting an immune response, comprising an isolated polypeptide and a physiologically acceptable carrier, the isolated polypeptide comprising an immunogenic portion of a prostate protein having a sequence of SEQ ID NO:3.

2. A composition for eliciting an immune response, comprising an isolated polypeptide and a non-specific immune response enhancer, the isolated polypeptide comprising an immunogenic portion of a prostate protein having a sequence of SEQ ID NO:3.

3. The composition of claim 2 wherein the non-specific immune response enhancer is an adjuvant.

* * * * *

```
                          SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
        (A) LENGTH: 89 amino acids
        (B) TYPE: amino acid
        (C) STRANDEDNESS:
        (D) TOPOLOGY: linear (xi) SEQUENCE DESCRIPTION: SEQ ID NO:1:

Ala Arg Ala Ser Val Met Leu Leu Gly Met Met Ala Arg Gly Lys Pro
1               5                   10                  15

Glu Ile Val Gly Ser Asn Leu Asp Thr Leu Met Ser Ile Gly Leu Asp
            20                  25                  30

Glu Lys Phe Pro Gln Asp Tyr Arg Leu Ala Gln Gln Val Cys His Ala
        35                  40                  45

Ile Ala Asn Ile Ser Asp Arg Arg Lys Pro Ser Leu Gly Lys Arg His
    50                  55                  60

Pro Pro Phe Arg Leu Pro Gln Glu His Arg Leu Phe Glu Arg Leu Arg
65                  70                  75                  80

Glu Thr Val Thr Lys Gly Phe Val His
                85

(2) INFORMATION FOR SEQ ID NO:2:

(i) SEQUENCE CHARACTERISTICS:
        (A) LENGTH: 89 amino acids
        (B) TYPE: amino acid
        (C) STRANDEDNESS:
        (D) TOPOLOGY: linear (xi) SEQUENCE DESCRIPTION: SEQ ID NO:2:

Ala Arg Gly Arg Phe Gly Arg Leu Gly Val Gly Gly Glu Pro His Pro
1               5                   10                  15

Arg Arg Asn Pro Ala Leu Pro Thr Glu Leu Ala Glu Leu Thr Pro Gln
            20                  25                  30

Val Arg Arg Ala Ala Xaa Lys Thr Gln Arg Ser Gln Val Lys Pro Arg
        35                  40                  45

His Arg Arg Gly Trp Pro Pro Thr Val Pro Leu Ala Gly Arg Leu Glu
    50                  55                  60

Glu Leu Lys Thr Pro Arg Ser Pro Arg Pro Pro Glu Gln Gly Leu Asp
65                  70                  75                  80

Pro Ser Pro Cys Ser Leu Pro Ser Pro
                85

(2) INFORMATION FOR SEQ ID NO:3:

(i) SEQUENCE CHARACTERISTICS:
        (A) LENGTH: 858 amino acids
```

(B) TYPE: amino acid
        (C) STRANDEDNESS:
        (D) TOPOLOGY: linear (xi) SEQUENCE DESCRIPTION: SEQ ID NO:3:

Gln Glu Ser Glu Pro Phe Ser His Ile Asp Pro Glu Ser Glu Glu
 1               5                  10                  15

Thr Arg Leu Leu Asn Ile Leu Gly Leu Ile Phe Lys Gly Pro Ala Ala
            20                  25                  30

Ser Thr Gln Glu Lys Asn Pro Arg Glu Ser Thr Gly Asn Met Val Thr
        35                  40                  45

Gly Gln Thr Val Cys Lys Asn Lys Pro Asn Met Ser Asp Pro Glu Glu
    50                  55                  60

Ser Arg Gly Asn Asp Glu Leu Val Lys Gln Glu Met Leu Val Gln Tyr
65                  70                  75                  80

Leu Gln Asp Ala Tyr Ser Phe Ser Arg Lys Ile Thr Glu Ala Ile Gly
                85                  90                  95

Ile Ile Ser Lys Met Met Tyr Glu Asn Thr Thr Thr Val Val Gln Glu
            100                 105                 110

Val Ile Glu Xaa Phe Val Met Val Phe Gln Phe Gly Val Pro Gln Ala
            115                 120                 125

Leu Phe Gly Val Arg Arg Met Leu Pro Leu Ile Trp Ser Lys Glu Pro
    130                 135                 140

Gly Val Arg Glu Ala Val Leu Asn Ala Tyr Arg Gln Leu Tyr Leu Asn
145                 150                 155                 160

Pro Lys Gly Asp Ser Ala Arg Ala Lys Ala Gln Ala Leu Ile Gln Asn
                165                 170                 175

Leu Ser Leu Leu Leu Val Asp Ala Ser Val Gly Thr Ile Gln Cys Leu
            180                 185                 190

Glu Glu Ile Leu Cys Glu Phe Val Gln Lys Asp Glu Leu Lys Pro Ala
        195                 200                 205

Val Thr His Leu Leu Trp Glu Arg Ala Thr Glu Lys Val Ala Cys Cys
    210                 215                 220

Pro Leu Glu Arg Cys Ser Ser Val Met Leu Leu Gly Met Met Ala Arg
225                 230                 235                 240

Arg Lys Pro Glu Ile Val Gly Ser Asn Leu Asp Thr Leu Met Ser Ile
                245                 250                 255

Gly Leu Asp Glu Lys Phe Pro Gln Asp Tyr Arg Leu Ala Gln Gln Val
            260                 265                 270

Cys His Ala Ile Ala Asn Ile Ser Asp Arg Arg Lys Pro Ser Leu Gly
        275                 280                 285

Lys Arg His Pro Pro Phe Arg Leu Pro Gln Glu His Arg Leu Phe Glu
    290                 295                 300

Arg Leu Arg Glu Thr Val Thr Lys Gly Phe Val His Pro Asp Pro Leu
305                 310                 315                 320

Trp Ile Pro Phe Lys Glu Val Ala Val Thr Leu Ile Tyr Gln Leu Ala
                325                 330                 335

Glu Gly Pro Glu Val Ile Cys Ala Gln Ile Leu Gln Gly Cys Ala Lys
            340                 345                 350

Gln Ala Leu Glu Lys Leu Glu Lys Arg Thr Ser Gln Glu Asp Pro
        355                 360                 365

Lys Glu Ser Pro Ala Met Leu Pro Thr Phe Leu Leu Met Asn Leu Leu
    370                 375                 380

Ser Leu Ala Gly Asp Val Ala Leu Gln Gln Leu Val His Leu Glu Gln

-continued

```
       385              390              395              400
Ala Val Ser Gly Glu Leu Cys Arg Arg Arg Val Leu Arg Glu Glu Gln
                405              410              415
Glu His Lys Thr Lys Asp Pro Lys Glu Lys Asn Thr Ser Ser Glu Thr
            420              425              430
Thr Met Glu Glu Glu Leu Gly Leu Val Gly Ala Thr Ala Asp Asp Thr
        435              440              445
Glu Ala Glu Leu Ile Arg Gly Ile Cys Glu Met Glu Leu Leu Asp Gly
    450              455              460
Lys Gln Thr Leu Ala Ala Phe Val Pro Leu Leu Lys Val Cys Asn
465              470              475              480
Asn Pro Gly Leu Tyr Ser Asn Pro Asp Leu Ser Ala Ala Ser Leu
                485              490              495
Ala Leu Gly Lys Phe Cys Met Ile Ser Ala Thr Phe Cys Asp Ser Gln
            500              505              510
Leu Arg Leu Leu Phe Thr Met Leu Glu Lys Ser Pro Leu Pro Ile Val
        515              520              525
Arg Ser Asn Leu Met Val Ala Thr Gly Asp Leu Ala Ile Arg Phe Pro
    530              535              540
Asn Leu Val Asp Pro Trp Thr Pro His Leu Tyr Ala Arg Leu Arg Asp
545              550              555              560
Pro Ala Gln Gln Val Arg Lys Thr Ala Gly Leu Val Met Thr His Leu
                565              570              575
Ile Leu Lys Asp Met Val Lys Val Lys Gly Gln Val Ser Glu Met Ala
            580              585              590
Val Leu Leu Ile Asp Pro Glu Pro Gln Ile Ala Ala Leu Ala Lys Asn
        595              600              605
Phe Phe Asn Glu Leu Ser His Lys Gly Asn Ala Ile Tyr Asn Leu Leu
    610              615              620
Pro Asp Ile Ile Ser Arg Leu Ser Asp Pro Glu Leu Gly Val Glu Glu
625              630              635              640
Glu Pro Phe His Thr Ile Met Lys Gln Leu Leu Ser Tyr Ile Thr Lys
                645              650              655
Asp Lys Gln Thr Glu Ser Leu Val Glu Lys Leu Cys Gln Arg Phe Arg
            660              665              670
Thr Ser Arg Thr Glu Arg Gln Gln Arg Asp Leu Ala Tyr Cys Val Ser
        675              680              685
Gln Leu Pro Leu Thr Glu Arg Gly Leu Arg Lys Met Leu Asp Asn Phe
    690              695              700
Asp Cys Phe Gly Asp Lys Leu Ser Asp Glu Ser Ile Phe Ser Ala Phe
705              710              715              720
Leu Ser Val Val Gly Lys Leu Arg Arg Gly Ala Lys Pro Glu Gly Lys
                725              730              735
Ala Ile Ile Asp Glu Phe Glu Gln Lys Leu Arg Ala Cys His Thr Arg
            740              745              750
Gly Leu Asp Gly Ile Lys Glu Leu Glu Ile Gly Gln Ala Gly Ser Gln
        755              760              765
Arg Ala Pro Ser Ala Lys Lys Pro Ser Thr Gly Ser Arg Tyr Gln Pro
    770              775              780
Leu Ala Ser Thr Ala Ser Asp Asn Asp Phe Val Thr Pro Glu Pro Arg
785              790              795              800
Arg Thr Thr Arg Arg His Pro Asn Thr Gln Gln Arg Ala Ser Lys Lys
                805              810              815
```

```
Lys Pro Lys Val Val Phe Ser Ser Asp Glu Ser Ser Glu Glu Asp Leu
            820                 825                 830

Ser Ala Glu Met Thr Glu Asp Glu Thr Pro Lys Lys Thr Thr Pro Ile
            835                 840                 845

Leu Arg Ala Ser Ala Arg Arg His Arg Ser
    850                 855

(2) INFORMATION FOR SEQ ID NO:4:

(i) SEQUENCE CHARACTERISTICS:
        (A) LENGTH: 127 amino acids
        (B) TYPE: amino acid
        (C) STRANDEDNESS:
        (D) TOPOLOGY: linear (xi) SEQUENCE DESCRIPTION: SEQ ID NO:4:

Ala Arg Asp Arg Leu Val Ala Ser Lys Thr Asp Gly Lys Ile Val Gln
1               5                   10                  15

Tyr Glu Cys Glu Gly Asp Thr Cys Gln Glu Lys Ile Asp Ala Leu
            20                  25                  30

Gln Leu Glu Tyr Ser Tyr Leu Leu Thr Ser Gln Leu Glu Ser Gln Arg
            35                  40                  45

Ile Tyr Trp Glu Asn Lys Ile Val Arg Ile Glu Lys Asp Thr Ala Glu
    50                  55                  60

Glu Ile Asn Asn Met Lys Thr Lys Phe Lys Glu Thr Ile Xaa Xaa Cys
65                  70                  75                  80

Asp Asn Leu Glu His Xaa Leu Asn Asp Leu Leu Lys Glu Lys Gln Ser
            85                  90                  95

Val Glu Arg Lys Cys Thr Gln Leu Asn Thr Lys Val Ala Lys Leu Thr
            100                 105                 110

Asn Glu Leu Lys Glu Glu Gln Glu Met Asn Lys Cys Leu Arg Ala
            115                 120                 125

(2) INFORMATION FOR SEQ ID NO:5:

(i) SEQUENCE CHARACTERISTICS:
        (A) LENGTH: 43 amino acids
        (B) TYPE: amino acid
        (C) STRANDEDNESS:
        (D) TOPOLOGY: linear (xi) SEQUENCE DESCRIPTION: SEQ ID NO:5:

Ala Arg Ala Glu Val Gln Arg Trp Arg Arg Leu Val Ala Gly Arg Arg
1               5                   10                  15

Arg Ala Gly Gly Asp Gly Gly Asn Ser Gly Ser Cys Ser Arg Trp Gly
            20                  25                  30

Gly Phe Thr Ser Tyr Pro Trp Asp Arg Glu Ile
            35                  40

(2) INFORMATION FOR SEQ ID NO:6:

(i) SEQUENCE CHARACTERISTICS:
        (A) LENGTH: 751 amino acids
        (B) TYPE: amino acid
        (C) STRANDEDNESS:
        (D) TOPOLOGY: linear (xi) SEQUENCE DESCRIPTION: SEQ ID NO:6:

Pro Ala Glu Ala His Ser Asp Ser Leu Ile Asp Thr Phe Pro Glu Cys
1               5                   10                  15
```

-continued

```
Ser Thr Glu Gly Phe Ser Ser Asp Ser Asp Leu Val Ser Leu Thr Val
             20                  25                  30

Asp Val Asp Ser Leu Ala Glu Leu Asp Asp Gly Met Ala Ser Asn Gln
             35                  40                  45

Asn Ser Pro Ile Arg Thr Phe Gly Leu Asn Leu Ser Ser Asp Ser Ser
 50                  55                  60

Ala Leu Gly Ala Val Ala Ser Asp Ser Glu Gln Ser Lys Thr Glu Glu
 65                  70                  75                  80

Glu Arg Glu Ser Arg Ser Leu Phe Pro Gly Ser Leu Lys Pro Lys Leu
                 85                  90                  95

Gly Lys Arg Asp Tyr Leu Glu Lys Ala Gly Glu Leu Ile Lys Leu Ala
             100                 105                 110

Leu Lys Lys Glu Glu Asp Asp Tyr Glu Ala Ala Ser Asp Phe Tyr
         115                 120                 125

Arg Lys Gly Val Asp Leu Leu Leu Glu Gly Val Gln Gly Glu Ser Ser
         130                 135                 140

Pro Thr Arg Arg Glu Ala Val Lys Arg Arg Thr Ala Glu Tyr Leu Met
145                 150                 155                 160

Arg Ala Glu Ser Ile Ser Ser Leu Tyr Gly Lys Pro Gln Leu Asp Asp
                 165                 170                 175

Val Ser Gln Pro Pro Gly Ser Leu Ser Ser Arg Pro Leu Trp Asn Leu
             180                 185                 190

Arg Ser Pro Ala Glu Glu Leu Lys Ala Phe Arg Val Leu Gly Val Ile
             195                 200                 205

Asp Lys Val Leu Leu Val Met Asp Thr Arg Thr Glu His Thr Phe Ile
         210                 215                 220

Leu Xaa Gly Leu Arg Lys Ser Ser Glu Tyr Ser Arg Asn Arg Lys Thr
225                 230                 235                 240

Ile Xaa Pro Arg Cys Val Pro Xaa Met Val Cys Leu His Lys Tyr Ile
             245                 250                 255

Ile Ser Glu Glu Ser Xaa Phe Leu Val Leu Gln His Ala Glu Xaa Gly
             260                 265                 270

Lys Leu Trp Ser Tyr Ile Ser Lys Phe Leu Asn Arg Ser Pro Glu Glu
             275                 280                 285

Ser Phe Asp Ile Lys Glu Val Lys Lys Pro Thr Leu Ala Lys Val His
 290                 295                 300

Leu Gln Gln Pro Thr Ser Ser Pro Gln Asp Ser Ser Ser Phe Glu Ser
305                 310                 315                 320

Arg Gly Ser Asp Gly Gly Ser Met Leu Lys Ala Leu Pro Leu Lys Ser
                 325                 330                 335

Ser Leu Thr Pro Ser Ser Gln Asp Asp Ser Asn Gln Glu Asp Asp Gly
             340                 345                 350

Gln Asp Ser Ser Pro Lys Trp Pro Asp Ser Gly Ser Ser Ser Glu Glu
             355                 360                 365

Glu Cys Thr Thr Ser Tyr Leu Thr Leu Cys Asn Glu Tyr Gly Gln Glu
         370                 375                 380

Lys Ile Glu Pro Gly Ser Leu Asn Glu Glu Pro Phe Met Lys Thr Glu
385                 390                 395                 400

Gly Asn Gly Val Asp Thr Lys Ala Ile Lys Ser Phe Pro Ala His Leu
                 405                 410                 415

Ala Ala Asp Ser Asp Ser Pro Ser Thr Gln Leu Arg Ala His Glu Leu
             420                 425                 430

Lys Phe Phe Pro Asn Asp Asp Pro Glu Ala Val Ser Ser Pro Arg Thr
```

-continued

```
                435                 440                 445
Ser Asp Ser Leu Ser Arg Ser Lys Asn Ser Pro Met Glu Phe Phe Arg
    450                 455                 460

Ile Asp Ser Lys Asp Ser Ala Ser Glu Leu Leu Gly Leu Asp Phe Gly
465                 470                 475                 480

Glu Lys Leu Tyr Ser Leu Lys Ser Glu Pro Leu Lys Pro Phe Phe Thr
                485                 490                 495

Leu Pro Asp Gly Asp Ser Ala Ser Arg Ser Phe Asn Thr Ser Glu Ser
            500                 505                 510

Lys Val Glu Phe Lys Ala Gln Asp Thr Ile Ser Arg Gly Ser Asp Asp
            515                 520                 525

Ser Val Pro Val Ile Ser Phe Lys Asp Ala Ala Phe Asp Asp Val Ser
    530                 535                 540

Gly Thr Asp Glu Gly Arg Pro Asp Leu Leu Val Asn Leu Pro Gly Glu
545                 550                 555                 560

Leu Glu Ser Thr Arg Glu Ala Ala Ala Met Gly Pro Thr Lys Phe Thr
                565                 570                 575

Gln Thr Asn Ile Gly Ile Ile Glu Asn Lys Leu Leu Glu Ala Pro Asp
            580                 585                 590

Val Leu Cys Leu Arg Leu Ser Thr Glu Gln Cys Gln Ala His Glu Glu
    595                 600                 605

Lys Gly Ile Glu Glu Leu Ser Asp Pro Ser Gly Pro Lys Ser Tyr Ser
610                 615                 620

Ile Thr Glu Lys His Tyr Ala Gln Glu Asp Pro Arg Met Leu Phe Val
625                 630                 635                 640

Ala Xaa Val Asp His Ser Ser Ser Gly Asp Met Ser Leu Leu Pro Ser
                645                 650                 655

Ser Asp Pro Lys Phe Gln Gly Leu Gly Val Val Glu Ser Xaa Val Thr
            660                 665                 670

Ala Asn Asn Thr Glu Glu Ser Leu Phe Arg Ile Cys Ser Pro Leu Ser
            675                 680                 685

Gly Ala Asn Glu Tyr Ile Ala Ser Thr Asp Thr Leu Lys Thr Glu Glu
    690                 695                 700

Val Leu Leu Phe Thr Asp Gln Thr Asp Asp Leu Ala Lys Glu Glu Pro
705                 710                 715                 720

Thr Ser Leu Phe Xaa Arg Asp Ser Glu Thr Lys Gly Glu Ser Gly Leu
                725                 730                 735

Val Leu Glu Gly Asp Lys Glu Ile His Gln Ile Phe Glu Gly Pro
            740                 745                 750
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:7:

```
Ala Arg Gly Ser Thr Gln
1               5
```

(2) INFORMATION FOR SEQ ID NO:8:

(i) SEQUENCE CHARACTERISTICS:
        (A) LENGTH: 16 amino acids
        (B) TYPE: amino acid (C) STRANDEDNESS:
        (D) TOPOLOGY: linear (xi) SEQUENCE DESCRIPTION: SEQ ID NO:8:

Ala Arg Gly Ser Ser Gln Val Arg Val Lys Ser Trp Arg Gly Asp Met
1               5                   10                  15

(2) INFORMATION FOR SEQ ID NO:9:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (xi) SEQUENCE DESCRIPTION: SEQ ID NO:9:

CCGCACGAGC CTCTGTCATG CTTCTTGGCA TGATGGCACG AGGAAAGCCA GAAATTGTGG     60

GAAGCAATTT AGACACACTG ATGAGCATAG GGCTGGATGA GAAGTTTCCA CAGGACTACA    120

GGCTGGCCCA GCAGGTGTGC CATGCCATTG CCAACATCTC GGACAGGAGA AAGCCTTCTC    180

TGGGCAAACG TCACCCCCCC TTCCGGCTGC CTCAGGAACA CAGGTTGTTT GAGCGACTGC    240

GGGAGACAGT CACAAAAGGC TTTGTCCACC C                                   271

(2) INFORMATION FOR SEQ ID NO:10:

(i) SEQUENCE CHARACTERISTICS:
        (A) LENGTH: 403 base pairs
        (B) TYPE: nucleic acid
        (C) STRANDEDNESS: single
        (D) TOPOLOGY: linear (xi) SEQUENCE DESCRIPTION: SEQ ID NO:10:

GGGTGGATAA CCTGAGGTAG GGAGTTCGAG ACCAGCCTGA CCAACATGGA GAAACCCCAT     60

CTCTACTAAA AATAAAAAAT TAGCCGGCGT ATTGGCGTGC GCCTGTAATC CCAGCTACTC    120

AAGAGGCTGA GGCAGGAGAA TCGCCTGAAC CCAGAGGCGG AGGTTGTAGT GAGCCGAAAT    180

CACACCATTG CACTCCAGCT TGGGCAACAA TAGCGAACCT CCATCTCAAA TTAAAAAAAA    240

AATGCCTACA CGCTTCTTTA AAATGCAAGG CTTTCTCTTA AATTAGCCTA ACTGAACTGC    300

GTTGAGCTGC TTCAACTTTG GAATATATGT TTGCCAATCT CCTTGTTTTC TAATGAATAA    360

ATGTTTTTAT ATACTTTTAA AAAAAAAAA AAAAAAACTC GAG                      403

(2) INFORMATION FOR SEQ ID NO:11:

(i) SEQUENCE CHARACTERISTICS:
        (A) LENGTH: 2276 base pairs
        (B) TYPE: nucleic acid
        (C) STRANDEDNESS: single
        (D) TOPOLOGY: linear (xi) SEQUENCE DESCRIPTION: SEQ ID NO:11:

GGAGGTTTGG GCGGCTTGGC GTCGGAGGAG AGCCCCACCC GCGGAGGAAC CCAGCCTTGC     60

CAACGGAGCT GGCGGAGCTC ACTCCTCAGG TCAGGCGGGC GGCGTANAAA ACGCAGCGGA    120

GCCAGGTGAA ACCAAGGCAC CGCCGTGGCT GGCCCCCGAC AGTTCCTCTA GCCGGGAGGT    180

TGGAGGAGCT GAAAACGCCG CGGAGCCCTC GGCCGCCCGA GCAGGGGCTG GACCCCAGCC    240

CTTGCAGCCT CCCTTCTCCT GGCACCCAAG TGCAGTCCTG GCTGCAGAAG GGGCCGCGGG    300

CGCACTGAGT TTCAACCTC CGTTCAGCCT GTCTGTCTCA GGGTGCAGCC TTAATGAGAG    360

GTGATTCCTA AGCTGCTGGG AACCTGAGGT TGTCAAAGGG GCGGCAGGAA ATGGACAGCA    420

```
GTATAAAACC CAGAAGCAGA ACTTGAAGGT TAAACCACTA GCCCATTTCA CAGAATGTTT      480

CATCCATTTG TGGACCAAAA GATGGAGTTG GTTTTTATTT TTAAAAAGAT AATGTTAATG      540

ATCTGATACC ACTACAAATA TTTACGTGAG AAGATTCATG GACTTGTCTT TTGGTTGGAC      600

TGTCACTCAT TTCTGAAAGT TTCTTCAGCC ACAATTTCTA TTTGAAAATT CAAGTATCAA      660

AGGATACCAG GTTTAGAATG GTATAATGAT GTATTTTGTC TGAGGACTGC AAATTTTATA      720

GAGACCACAG TTGGATTCCA GTGATATTCT GCAATCAAAG TGATTTGATA AACCTAATTT      780

TGAAGCATTT TATATTTATA AGCGACATCA AAAGATGGGA GAAAAAAATG GCGATGCAAA      840

AACTTTCTGG ATGGAGCTAG AAGATGATGG AAAAGTGGAC TTCATTTTTG AACAAGTACA      900

AAATGTGCTG CAGTCACTGA ACAAAAGAT CAAAGATGGG TCTGCCACCA ATAAAGAATA      960

CATCCAAGCA ATGATTCTAG TGAATGAAGC AACTATAATT AACAGTTCAA CATCAATAAA     1020

GGATCCTATG CCTGTGACTC AGAAGGAACA GGAAAACAAA TCCAATGCAT TTCCCTCTAC     1080

ATCATGTGAA AACTCCTTTC CAGAAGACTG TACATTTCTA ACAACAGGAA ATAAGGAAAT     1140

TCTCTCTCTT GAAGATAAAG TTGTAGACTT TAGAGAAAAA GACTCATCTT CGAATTTATC     1200

TTACCAAAGT CATGACTGCT CTGGTGCTTG TCTGATGAAA ATGCCACTGA ACTTGAAGGG     1260

AGAAAACCCT CTGCAGCTGC CAATCAAATG TCACTTCCAA AGACGACATG CAAAGACAAA     1320

CTCTCATTCT TCAGCACTCC ACGTGAGTTA TAAAACCCCT TGTGGAAGGA GTCTACGAAA     1380

CGTGGAGGAA GTTTTTCGTT ACCTGCTTGA GACAGAGTGT AACTTTTTAT TTACAGATAA     1440

CTTTTCTTTC AATACCTATG TTCAGTTGGC TCGGAATTAC CCAAAGCAAA AGAAGTTGT      1500

TTCTGATGTG GATATTAGCA ATGGAGTGGA ATCAGTGCCC ATTTCTTTCT GTAATGAAAT     1560

TGACAGTAGA AAGCTCCCAC AGTTTAAGTA CAGAAAGACT GTGTGGCCTC GAGCATATAA     1620

TCTAACCAAC TTTTCCAGCA TGTTTACTGA TTCCTGTGAC TGCTCTGAGG GCTGCATAGA     1680

CATAACAAAA TGTGCATGTC TTCAACTGAC AGCAAGGAAT GCCAAAACTT CCCCCTTGTC     1740

AAGTGACAAA ATAACCACTG GATATAAATA TAAAAGACTA CAGAGACAGA TTCCTACTGG     1800

CATTTATGAA TGCAGCCTTT TGTGCAAATG TAATCGACAA TTGTGTCAAA ACCGAGTTGT     1860

CCAACATGGT CCTCAAGTGA GGTTACAGGT GTTCAAAACT GAGCAGAAGG GATGGGGTGT     1920

ACGCTGTCTA GATGACATTG ACAGAGGGAC ATTTGTTTGC ATTTATTCAG GAAGATTACT     1980

AAGCAGAGCT AACACTGAAA AATCTTATGG TATTGATGAA AACGGGAGAG ATGAGAATAC     2040

TATGAAAAAT ATATTTTCAA AAAAGAGGAA ATTAGAAGTT GCATGTTCAG ATTGTGAAGT     2100

TGAAGTTCTC CCATTAGGAT TGGAAACACA TCCTAGAACT GCTAAAACTG AGAAATGTCC     2160

ACCAAAGTTC AGTAATAATC CCAAGGAGCT TACTATGGAA ACGAAATATG ATAATATTTC     2220

AAGAATTCAG TATCATTCAG TTATTAGAGA TCCTGAATCC AAGACAGCCA TTTTTC        2276

(2) INFORMATION FOR SEQ ID NO:12:

(i) SEQUENCE CHARACTERISTICS:
        (A) LENGTH: 3114 base pairs
        (B) TYPE: nucleic acid
        (C) STRANDEDNESS: single
        (D) TOPOLOGY: linear (xi) SEQUENCE DESCRIPTION: SEQ ID NO:12:

CAGGAGTCCG AACCCTTCAG TCATATAGAC CCAGAGGAGT CAGAGGAGAC CAGGCTCTTG       60

AATATCTTAG GACTTATCTT CAAAGGCCCA GCAGCTTCCA CACAAGAAAA GAATCCCCGG      120

GAGTCTACAG GAAACATGGT CACAGGACAG ACTGTCTGTA AAAATAAACC CAATATGTCG      180
```

```
-continued

GATCCTGAGG AATCCAGGGG AAATGATGAA CTAGTGAAGC AGGAGATGCT GGTACAGTAT      240

CTGCAGGATG CCTACAGCTT CTCCCGGAAG ATTACAGAGG CCATTGGCAT CATCAGCAAG      300

ATGATGTATG AAAACACAAC TACAGTGGTG CAGGAGGTGA TTGAATNCTT TGTGATGGTC      360

TTCCAATTTG GGGTACCCCA GGCCCTGTTT GGGGTGCGCC GTATGCTGCC TCTCATCTGG      420

TCTAAGGAGC CTGGTGTCCG GGAAGCCGTG CTTAATGCCT ACCGCCAACT CTACCTCAAC      480

CCCAAAGGGG ACTCTGCCAG AGCCAAGGCC CAGGCTTTGA TTCAGAATCT CTCTCTGCTG      540

CTAGTGGATG CCTCGGTTGG GACCATTCAG TGTCTTGAGG AAATTCTCTG TGAGTTTGTG      600

CAGAAGGATG AGTTGAAACC AGCAGTGACC CATCTGCTGT GGGAGCGGGC CACCGAGAAG      660

GTCGCCTGCT GTCCTCTGGA GCGCTGTTCC TCTGTCATGC TTCTTGGCAT GATGGCACGA      720

AGAAAGCCAG AAATTGTGGG AAGCAATTTA GACACACTGA TGAGCATAGG GCTGGATGAG      780

AAGTTTCCAC AGGACTACAG GCTGGCCCAG CAGGTGTGCC ATGCCATTGC CAACATCTCG      840

GACAGGAGAA AGCCTTCTCT GGGCAAACGT CACCCCCCCT TCCGGCTGCC TCAGGAACAC      900

AGGTTGTTTG AGCGACTGCG GGAGACAGTC ACAAAAGGCC TTGTCCACCC AGACCCACTC      960

TGGATCCCAT TCAAAGAGGT GGCAGTGACC CTCATTTACC AACTGGCAGA GGGCCCCGAA     1020

GTGATCTGTG CCCAGATATT GCAGGGCTGT GCAAAACAGG CCCTGGAGAA GCTAGAAGAG     1080

AAGAGAACCA GTCAGGAGGA CCCGAAGGAG TCCCCCGCAA TGCTCCCCAC TTTCCTGTTG     1140

ATGAACCTGC TGTCCCTGGC TGGGGATGTG GCTCTGCAGC AGCTGGTCCA CTTGGAGCAG     1200

GCAGTGAGTG GAGAGCTCTG CCGGCGCCGA GTTCTCCGGG AAGAACAGGA GCACAAGACC     1260

AAAGATCCCA AGGAGAAGAA TACGAGCTCT GAGACCACCA TGGAGGAGGA GCTGGGGCTG     1320

GTTGGGGCAA CAGCAGATGA CACAGAGGCA GAACTAATCC GTGGCATCTG CGAGATGGAA     1380

CTGTTGGATG GCAAACAGAC ACTGGCTGCC TTTGTTCCAC TCTTGCTTAA AGTCTGTAAC     1440

AACCCAGGCC TCTATAGCAA CCCAGACCTC TCTGCAGCTG CTTCACTTGC CCTTGGCAAG     1500

TTCTGCATGA TCAGTGCCAC TTTCTGCGAC TCCCAGCTTC GTCTTCTGTT CACCATGCTG     1560

GAAAAGTCTC CACTTCCCAT TGTCCGGTCT AACCTCATGG TTGCCACTGG GGATCTGGCC     1620

ATCCGCTTTC CCAATCTGGT GGACCCCTGG ACTCCTCATC TGTATGCTCG CCTCCGGGAC     1680

CCTGCTCAGC AAGTGCGGAA AACAGCGGGG CTGGTGATGA CCCACCTGAT CCTCAAGGAC     1740

ATGGTGAAGG TGAAGGGGCA GGTCAGTGAG ATGGCGGTGC TGCTCATCGA CCCCGAGCCT     1800

CAGATTGCTG CCCTGGCCAA GAACTTCTTC AATGAGCTCT CCCACAAGGG CAACGCAATC     1860

TATAATCTCC TTCCAGATAT CATCAGCCGC CTGTCAGACC CCGAGCTGGG GGTGGAGGAA     1920

GAGCCTTTCC ACACCATCAT GAAACAGCTC CTCTCCTACA TCACCAAGGA CAAGCAGACA     1980

GAGAGCCTGG TGGAAAAGCT GTGTCAGCGG TTCCGCACAT CCCGAACTGA GCGGCAGCAG     2040

CGAGACCTGG CCTACTGTGT GTCACAGCTG CCCCTCACAG AGCGAGGCCT CCGTAAGATG     2100

CTTGACAATT TTGACTGTTT TGGAGACAAA CTGTCAGATG AGTCCATCTT CAGTGCTTTT     2160

TTGTCAGTTG TGGGCAAGCT GCGACGTGGG GCCAAGCCTG AGGGCAAGGC TATAATAGAT     2220

GAATTTGAGC AGAAGCTTCG GGCCTGTCAT ACCAGAGGTT TGGATGGAAT CAAGGAGCTT     2280

GAGATTGGCC AAGCAGGTAG CCAGAGAGCG CCATCAGCCA AGAAACCATC CACTGGTTCT     2340

AGGTACCAGC CTCTGGCTTC TACAGCCTCA GACAATGACT TTGTCACACC AGAGCCCCGC     2400

CGTACTACCC GTCGGCATCC AAACACCCAG CAGCGAGCTT CCAAAAAGAA ACCCAAAGTT     2460

GTCTTCTCAA GTGATGAGTC CAGTGAGGAA GATCTTTCAG CAGAGATGAC AGAAGACGAG     2520

ACACCCAAGA AAACAACTCC CATTCTCAGA GCATCGGCTC GCAGGCACAG ATCCTAGGAA     2580
```

```
GTCTGTTCCT GTCCTCCCTG TGCAGGGTAT CCTGTAGGGT GACCTGGAAT TCGAATTCTG    2640

TTTCCCTTGT AAAATATTTG TCTGTCTCTT TTTTTTAAAA AAAAAAAAGG CCGGGCACTG    2700

TGGCTCACGC CTGTAATCCC AGCACTTTGC GATACCAAGG CGGGTGGATA ACCTGAGGTA    2760

GGGAGTTCGA GACCAGCCTG ACCAACATGG AGAAACCCCA TCTCTACTAA AATAAAAAA    2820

TTAGCCGGGC GTATTGGCGT GCGCCTGTAA TCCCAGCTAC TCAAGAGGCT GAGGCAGGAG    2880

AATCGCCTGA ACCCAGAGGC GGAGGTTGTA GTGAGCCGAA ATCACACCAT TGCACTCCAG    2940

CTTGGGCAAC AATAGCGAAC CTCCATCTCA AATTAAAAAA AAAATGCCTA CACGCTCTTT    3000

AAAATGCAAG CTTTCTCTT AAATTAGCCT AACTGAACTG CGTTGAGCTG CTTCAACTTT    3060

GGAATATATG TTTGCCAATC TCCTTGTTTT CTAATGAATA AATGTTTTTA TATA          3114

(2) INFORMATION FOR SEQ ID NO:13:

(i) SEQUENCE CHARACTERISTICS:
        (A) LENGTH: 1797 base pairs
        (B) TYPE: nucleic acid
        (C) STRANDEDNESS: single
        (D) TOPOLOGY: linear (xi) SEQUENCE DESCRIPTION: SEQ ID NO:13:

CGGCACGAGA TCGACTGGTT GCAAGTAAAA CAGATGGAAA AATAGTACAG TATGAATGTG      60

AGGGGGATAC TTGCCAGGAA GAGAAAATAG ATGCCTTACA GTTAGAGTAT TCATATTTAC     120

TAACAAGCCA GCTGGAATCT CAGCGAATCT ACTGGGAAAA CAAGATAGTT CGGATAGAGA     180

AGGACACAGC AGAGGAAATT AACAACATGA AGACCAAGTT TAAAGAAACA ATTGAGAAGT     240

GTGATAATCT AGAGCACAAA CTAAATGATC TCCTAAAAGA AAAGCAGTCT GTGGAAAGAA     300

AGTGCACTCA GCTAAACACA AAAGTGGCCA AACTCACCAA CGAGCTCAAA GAGGAGCAGG     360

AAATGAACAA GTGTTTGCGA GCCAACCAAG TCCTCCTGCA GAACAAGCTA AAAGAGGAGG     420

AGAGGGTGCT GAAGGAGACC TGTGACCAAA AAGATCTGCA GATCACCGAG ATCCAGGAGC     480

AGCTGCGTGA CGTCATGTTC TACCTGGAGA CACAGCAGAA GATCAACCAT CTGCCTGCCG     540

AGACCCGGCA GGAAATCCAG GAGGGACAGA TCAACATCGC CATGGCCTCG GCCTCGAGCC     600

CTGCCTCTTC GGGGGGCAGT GGGAAGTTGC CCTCCAGGAA GGGCCGCAGC AAGAGGGGCA     660

AGTGACCTTC AGAGCAACAG ACATCCCTGA GACTGTTCTC CCTGACACTG TGAGAGTGTG     720

CTGGGACCTT CAGCTAAATG TGAGGGTGGG CCCTAATAAG TACAAGTGAG GATCAAGCCA     780

CAGTTGTTTG GCTCTTTCAT TTGCTAGTGT GTGATGTANT GAATGTAAAG GGTGCTGACT     840

GGAGAGCTGA TAGAAAGGCG CTGCGTTCGA AAAGGTCTTA ANAGTTCACT AACCTCACAT     900

TCTAATGACC ATTTTGCCTT CCTGCTTGGT AGAAGCCCCA ACTCTGCTGT GCATTTTTCC     960

ATTGTATTTA TGGAGTTGGC GTATTTGACA TTCAGTTCTG GGGTAGGTTT AAGATGTTAA    1020

GTTATTTCTT GTAACCTCAA AGGTAAGGTT ATCTAGCACT AAAGCACCAA ACCTCTCTGA    1080

GGGCATAACA GCTGCTTTAA AGAGAGGTTT CCATTGGCTA TTAAGGAGTT ATGAAAACTC    1140

CCTAGCAATA GTGTCATATC ATTATCATCT CCCCCTTCCT CTGGGGAGTG GAAGAATTGC    1200

TTGAATGTTA TCTGAAAAGA GGCCTGGTAG TAAACCAGGC CCTGGCTCTT TACCAGCAGT    1260

CATCTCTTCT TGCTCTGGGG CCAGCCAGGA AAAACAAACA ACCCGGGGCA CATTGGGTAG    1320

ACTCAGTGTA GGAAAAATGG TGGCAGCTCC ACTGTTTATT TTTGGTGACT TCGTACGTCA    1380

TTATGAACCG CAATTAAGGA GGAGGCTTAA TGGCTGTTCC CAAACTCAAA TCTCAGAGTG    1440

GGTATCCTAG CATCTAGCAA NACTGAGTGG GGAGATTTCT CATCCGTGTG AAAATGTAGA    1500
```

```
GTGAGGCCTC TGACTAGCTN ATTGTGTATT TTGTTGGGTT TAGTATTTTC TAAATGTTTA      1560

CAAAATATTG GGCTGCATGT TCAGGTTGCA GCTANAGGGA GCTTGGGCAN ATTTTCAATT      1620

ACGCTTTCAA GATATAACCA AAAGCTGTTT CTAAATCCTA AAATTAGAAT TTCAACAGAN     1680

CCCCCTTTAG AACAGTCATA TAACGCTTGT GTGGGCCAAC AGANGGGCTG TGTACTCTCT     1740

CTGGAACCAT AAATGTCAAA TAATTTATAA CCTGCANTAA TTGAGCAACT TAAATAA        1797

(2) INFORMATION FOR SEQ ID NO:14:

(i) SEQUENCE CHARACTERISTICS:
          (A) LENGTH: 720 base pairs
          (B) TYPE: nucleic acid
          (C) STRANDEDNESS: single
          (D) TOPOLOGY: linear (xi) SEQUENCE DESCRIPTION: SEQ ID NO:14:

TAATCACCAT CTGTTTTTGT GGGATGTGCT GCAGCATTTC CCAAAAAACT TNACGTGTAA       60

TGTTGCAAAA TGAATGTACT CAGACATTNT TAATTTTTAC TTAGGGCAGA CCAACTCTTT     120

GAGTCTCTCT TGGACTTATA TATACAGATA TCTTAAGAGT GGGAATGTAA AGCATAACCT     180

AATTNTCTTT CCTATAGAGA TTCTATTTTA TTTAAAATNT ATTTNTACAC TAGTTAGAAT     240

CCTGCTGTTT TGGCCAAGTA CTTGTCTTGC ATGTCTGACC TTGCAGAAGC TGGGGTGGAT     300

CATAGCATAC TAATGAAGAG AATTAGAAGT AGTTTACAAA GCTCGCTCAC TCCTCATTTC     360

TCTGTGATCC CTTCTATCCA GTGGCCCCAC CACCACCTGG GAAAACAGAT TTTTCAGTAC     420

AGGTGGGATA AATGCTCTGA AAGGCTGTGC CCAGAGGAAT GAGCAAATAG GCAAGTGTTT     480

CCAAACTACT TGGAGGTTTA CAAAAAATAT GTCCCAGAAA AAAAAAAAAT CTTACCAAGA     540

TACGTAAAGA AAAAAAAATT TTTTTTAAA CAGTCAAAGA GTCATGTTTG AATTTCACAA      600

AATCACATCA GACAGAAGTT GTTTTCTTCA GGAGGGAAAT GAACCACTTA ATATACCCAT     660

ACTACCTTGA ACAATGAAAT TGAATTAAAA TAGCCAAACT TTGAAAAAAA AAAAAAAAA      720

(2) INFORMATION FOR SEQ ID NO:15:

(i) SEQUENCE CHARACTERISTICS:
          (A) LENGTH: 1996 base pairs
          (B) TYPE: nucleic acid
          (C) STRANDEDNESS: single
          (D) TOPOLOGY: linear (xi) SEQUENCE DESCRIPTION: SEQ ID NO:15:

CAGAAGTGCA GCGGTGGCGG CGGCTGGTTG CGGGCCGGCG GCGGGCTGGC GGAGATGGAG       60

GTAACTCAGG ATCTTGTTCA AGATGGGGTG GCTTCACCAG CTACCCCTGG GACCGGGAAA     120

TCTAAGCTGG AAACATTGCC CAAAGAAGAC CTCATCAAGT TGCCAAGAA ACAGATGATG      180

CTAATACAGA AAGCTAAATC AAGGTGTACA GAATTGGAGA AAGAAATTGA AGAACTCAGA     240

TCAAAACCTG TTACTGAAGG AACTGGTGAT ATTATTAAGG CATTAACTGA ACGTCTGGAT     300

GCTCTTCTTC TGGAAAAAGC AGAGACTGAG CAACAGTGTC TTTCTCTGAA AAAGGAAAAT     360

ATAAAAATGA AGCAAGAGGT TGAGGATTCT GTAACAAAGA TGGGAGATGC ACATAAGGAG     420

TTGGAACAAT CACATATAAA CTATGTGAAA GAAATTGAAA ATTTGAAAAA TGAGTTGATG     480

GCAGTACGTT CCAAATACAG TGAAGACAAA GCTAACTTAC AAAAGCAGCT GGAAGAACAA     540

TGAATACGCA ATTAGAACTT TCAGAACAAC TTAAATTTCA GAACAACTCT GAAGATAATG     600

TTAAAAAACT ACAAGAAGAG ATTGAGAAAA TTAGGCCAGG CTTTGAGGAG CAAATTTTAT     660
```

```
ATCTGCAAAA GCAATTAGAC GCTACCACTG ATGAAAAGAA GGAAACAGTT ACTCAACTCC      720

AAAATATCAT TGAGGCTAAT TCTCAGCATT ACCAAAAAAA TATTAATAGT TTGCAGGAAG      780

AGCTTTTACA GTTGAAAGCT ATACACCAAG AAGAGGTGAA AGAGTTGATG TGCCAGATTG      840

AAGCATCAGC TAAGGAACAT GAAGCAGAGA TAAATAAGTT GAACGAGCTA AAAGAGAACT      900

TAGTAAAACA ATGTGAGGCA AGTGAAAAGA ACATCCAGAA GAAATATGAA TGTGAGTTAG      960

AAAATTTAAG GAAAGCCACC TCAAATGCAA ACCAAGACAA TCAGATATGT TCTATTCTCT     1020

TGCAAGAAAA TACATTTGTA GAACAAGTAG TAAATGAAAA AGTCAAACAC TTAGAAGATA     1080

CCTTAAAAGA ACTTGAATCT CAACACAGTA TCTTAAAAGA TGAGGTAACT TATATGAATA     1140

ATCTTAAGTT AAAACTTGAA ATGGATGCTC AACATATAAA GGATGAGTTT TTTCATGAAC     1200

GGGAAGACTT AGAGTTTAAA ATTAATGAAT TATTACTAGC TAAAGAAGAA CAGGGCTGTG     1260

TAATTGAAAA ATTAAAATCT GAGCTAGCAG GTTTAAATAA ACAGTTTTGC TATACTGTAG     1320

AACAGCATAA CAGAGAAGTA CAGAGTCTTA AGGAACAACA TCAAAAGAA ATATCAGAAC     1380

TAAATGAGAC ATTTTTGTCA GATTCAGAAA AGAAAAATT AACATTAATG TTTGAAATAC     1440

AGGGTCTTAA GGAACAGTGT GAAAACCTAC AGCAAGAAAA GCAAGAAGCA ATTTTAAATT     1500

ATGAGAGTTT ACGAGAGATT ATGGAAATTT TACAAACAGA ACTGGGGGAA TCTGCTGGAA     1560

AAATAAGTCA AGAGTTCGAA TCAATGAAGC AACAGCAAGC ATCTGATGTT CATGAACTGC     1620

AGCAGAAGCT CAGAACTGCT TTTACTGAAA AAGATGCCCT TCTCGAAACT GTGAATCGCC     1680

TCCAGGGAGA AAATGAAAAG TTACTATCTC AACAAGAATT GGTACCAGAA CTTGAAAATA     1740

CCATAAAGAA CCTTCAAGAA AAGAATGGAG TATACTTACT TAGTCTCAGT CAAAGAGATA     1800

CCATGTTAAA AGAATTAGAA GGAAAGATAA ATTCTCTTAC TGAGGAAAAA GATGATTTTA     1860

TAAATAAACT GAAAAATTCC CATGAAGAAA TGGATAATTT CCATAAGAAA TGTGAAAGGG     1920

AAGAAAGATT GATTCTTGAA CTTGGGAAGA AAGTAGAGCA AACTATCCAG TACAACAGTG     1980

AACTAGAACA AAAGGT                                                     1996

(2) INFORMATION FOR SEQ ID NO:16:

(i) SEQUENCE CHARACTERISTICS:
        (A) LENGTH: 3642 base pairs
        (B) TYPE: nucleic acid
        (C) STRANDEDNESS: single
        (D) TOPOLOGY: linear (xi) SEQUENCE DESCRIPTION: SEQ ID NO:16:

GTCCTGCTGA AGCTCACTCA GATTCCCTCA TTGATACCTT TCCTGAGTGT AGTACGGAAG       60

GCTTCTCCAG TGACAGTGAT CTGGTATCTC TTACTGTTGA TGTGGATTCT CTTGCTGAGT      120

TAGATGATGG AATGGCTTCC AATCAAAATT CTCCCATTAG AACTTTTGGT CTCAATCTTT      180

CTTCGGATTC TTCAGCACTA GGGGCTGTTG CTTCTGACAG TGAACAGAGC AAAACAGAAG      240

AAGAACGGGA AAGTCGTAGC CTCTTTCCTG GCAGTTTAAA GCCGAAGCTT GGCAAGAGAG      300

ATTATTTGGA GAAAGCAGGA GAATTAATAA AGCTGGCTTT AAAAAAGGAA GAAGAAGACG      360

ACTATGAAGC TGCTTCTGAT TTTTATAGGA AGGGAGTTGA TTTACTCCTA GAAGGTGTTC      420

AAGGAGAGTC AAGCCCTACC CGTCGAGAAG CTGTGAAGAG AAGAACAGCC GAGTACCTCA      480

TGCGGGCAGA AAGTATCTCT AGTCTTTATG GAAACCTCA GCTTGATGAT GTATCTCAGC      540

CTCCAGGATC ACTAAGTTCA AGGCCCCTTT GGAACCTAAG GAGCCCTGCC GAGGAGCTGA      600

AGGCCTTCAG AGTCCTTGGG GTGATTGACA AGGTTTTACT TGTAATGGAC ACAAGGACAG      660
```

-continued

```
AACACACTTT CATTTTAANA GGTCTAAGGA AAAGCAGTGA ATACAGCAGG AACAGAAAGA      720

CCATCCNCCC CCGCTGTGTG CCCANCATGG TGTGTCTGCA TAAGTACATC ATCTCTGAAG      780

AGTCANTATT TCTTGTGCTG CAGCATGCGG AANGTGGCAA ACTGTGGTCA TATATCAGTA      840

AATTTCTAAA CAGAAGTCCT GAAGAAAGCT TTGACATCAA GGAAGTGAAA AAACCTACAC      900

TTGCAAAAGT TCACCTGCAG CAGCCAACTT CTAGTCCTCA GGACAGCAGT AGCTTTGAAT      960

CCAGAGGAAG TGATGGTGGA AGCATGCTTA AGCTCTGCC TTTGAAGAGT AGTCTTACTC      1020

CAAGTTCTCA AGATGACAGC AACCAGGAAG ATGATGGCCA AGATAGCTCT CCAAAGTGGC     1080

CAGATTCTGG TTCAAGTTCA GAAGAAGAAT GTACTACTAG TTATTTAACA TTATGCAATG     1140

AATATGGGCA AGAAAAGATT GAACCAGGGT CTTTGAATGA GGAGCCCTTC ATGAAGACTG     1200

AAGGGAATGG TGTTGATACA AAAGCTATTA AAAGCTTCCC AGCACACCTT GCTGCTGACA     1260

GTGACAGCCC CAGCACACAG CTGAGAGCTC ACGAGCTGAA GTTCTTCCCC AACGATGACC     1320

CAGAAGCAGT TAGTTCTCCA AGAACATCAG ATTCCCTCAG TAGATCAAAA AATAGCCCCA     1380

TGGAATTCTT TAGGATAGAC AGTAAGGATA GCGCAAGTGA ACTCCTGGGA CTTGACTTTG     1440

GAGAAAAATT GTATAGTCTA AAATCAGAAC CTTTGAAACC ATTCTTTACT CTTCCAGATG     1500

GAGACAGTGC TTCTAGGAGT TTTAATACTA GTGAAAGCAA GGTAGAGTTT AAAGCTCAGG     1560

ACACCATTAG CAGGGGCTCA GATGACTCAG TGCCAGTTAT TTCATTTAAA GATGCTGCTT     1620

TTGATGATGT CAGTGGTACT GATGAAGGAA GACCTGATCT TCTTGTAAAT TTACCTGGTG     1680

AATTGGAGTC AACAAGAGAA GCTGCAGCAA TGGGACCTAC TAAGTTTACA CAAACTAATA     1740

TAGGGATAAT AGAAAATAAA CTCTTGGAAG CCCCTGATGT TTTATGCCTC AGGCTTAGTA     1800

CTGAACAATG CCAAGCACAT GAGGAGAAAG GCATAGAGGA ACTGAGTGAT CCCTCTGGGC     1860

CCAAATCCTA TAGTATAACA GAGAAACACT ATGCACAGGA GGATCCCAGG ATGTTATTTG     1920

TAGCANCTGT TGATCATAGT AGTTCAGGAG ATATGTCTTT GTTACCCAGC TCAGATCCTA     1980

AGTTTCAAGG ACTTGGAGTG GTTGAGTCAN CAGTAACTGC AAACAACACA GAAGAAAGCT     2040

TATTCCGTAT TTGTAGTCCA CTCTCAGGTG CTAATGAATA TATTGCAAGC ACAGACACTT     2100

TAAAAACAGA AGAAGTATTG CTGTTTACAG ATCAGACTGA TGATTTGGCT AAAGAGGAAC     2160

CAACTTCTTT ATTCCANAGA GACTCTGAGA CTAAGGGTGA AAGTGGTTTA GTGCTAGAAG     2220

GAGACAAGGA AATACATCAG ATTTTTGAAG GACCTTGATA AAAAATTAGC ACTANCCTCC     2280

AGGTTTTACA TCCCAGAGGG CTGCATTCAA AGNTGGGCAG CTGAAATGGT GGTAGCCCTT     2340

NGATGCTTTA ACATAGAGAG GGAATTGTGT GCCGCGATTG AACCCAAACA ANATNTTATT     2400

GAATGATAGA GGACACATTC AGNTAACGTA TTTTAGCAGG TGGAGTGAGG TTGAAGATTC     2460

CTGTGACAGC GATGCCATAG AGAGAATGTA CTGTGCCCCA GAGGTTGGAG CAATCACTGA     2520

AGAAACTGAA GCCTGTGATT GGTGGAGTTT GGGTGCTGTC CTCTTTGAAC TTNTCACTGG     2580

CAAGACTCTG GTTAATGCC ATCCAGCAGG AATAAATACT CACACTACTT TGAACATGCC      2640

AGAATGTGTC TCTGAAGAGG CTCGCTCACT CATTCAACAG CTCTTGCAGT TCAATCCTCT     2700

GGAACGACTT GGTGCTGGAG TTGCTGGTGT TGAAGATATC AAATCTCATC CATTTTTTAC     2760

CCCTGTGGAT TGGGCAGAAC TGATGAGATG AACGTAATGC AGGGTTATCT TCACACATTC     2820

TGATCTTCTC TGTGACAGGC ATCTCCAGCA CTGAGGCACC TCTGACTCAC AGTTACTTAT     2880

GGAGCACCAA AGCATTTGGA TAAGGACCGT TATAGGAAAT GGGGGGGAAA TGGCTAAAAG     2940

AGAACAATTT GTTTACAATT ACAAGATATT AGCTAATTGT GCCAGGGGCT GTTATATACA     3000

TATATACACA ACCAAGGTGT GATCTGAATT TAATCCACAT TTGGTGTTGC AGATGAGTTG     3060
```

-continued

```
TAAAGCCAAC TGAAAGAGTT CCTTCAAGAA GTTCCTCTGA TAGGAAGCTA GAAGTGTAGA      3120

ATGAAGTTTT ACTTGACAGA AGGACCTTTA CATGGCAGCT AACAGTGCTT TTTGCTGACC      3180

AGGATTGGTT TATATGATTA AATTAATATT TGCTTAATAA TACACTAAAA GTATATGAAC      3240

AATGTCATCA ATGAAACTTA AAAGCGAGAA AAAAGAATAT ACACATAATT TCTGACGGAA      3300

AACCTGTACC CTGATGCTGT ATAATGTATG TTGAATGTGG TCCCAGATTA TTTCTGTAAG      3360

AAGACACTCC ATGTTGTCAG CTTTGTACTC TTTGTTGATA CTGCTTATTT AGAGAAGGGT      3420

TCATATAAAC ACTCACTCTG TGTCTTCAAC AGCATCTTTC TTTCCCCATC TTTCTATTTT      3480

CTGCACCCTC TGCTTGTTCC CTCATATTCT GTTCTTCCGA CTCCTGCTAA CACACATGCA      3540

ACAAAAAAGG GAAGGGAGTG CTTATTTCCC TTTGTGTAAG GACTAAGAAA TCATGATATC      3600

AAATAAACAT GGTGAAACAT TNANAAAAAA AAAAAAAAAA AA                        3642
```

(2) INFORMATION FOR SEQ ID NO:17:

(i) SEQUENCE CHARACTERISTICS:
        (A) LENGTH: 1397 base pairs
        (B) TYPE: nucleic acid
        (C) STRANDEDNESS: single
        (D) TOPOLOGY: linear (xi) SEQUENCE DESCRIPTION: SEQ ID NO:17:

```
GTTCAACTCA ATAGAAGATG ACGTTTGCCA GCTAGTGTAT GTGGAAAGAG CTGAAGTGCT        60

CAAATCTGAA GATGGCGCCA GCCTCCCAGT GATGGACCTG ACTGAACTCC CCAAGTGCAC       120

GGTGTGTCTG GAGCGCATGG ACGAGTCTGT GAATGGCATC CTCACAACGT TATGTAACCA       180

CATCTTCCAC AGCCAGTGTC TACAGCGCTG GGACGATACC ACGTGTCCTG TTTGCCGGTA       240

CTGTCAAACG CCCGAGCCAG TAGAAGAAAA TAAGTGTTTT GAGTGTGGTG TTCAGGAAAA       300

TCTTTGGATT TGTTTAATAT GCGGCCACAT AGGATGTGGA CGGTATGTCA GTCGACATGC       360

TTATAAGCAC TTTGAGGAAA CGCAGCACAC GTATGCCATG CAGCTTACCA ACCATCGAGT       420

CTGGGACTAT GCTGGAGATA ACTATGTTCA TCGACTGGTT GCAAGTAAAA CAGATGGAAA       480

AATAGTACAG TATGAATGTG AGGGGATAC TTGCCAGGAA GAGAAAATAG ATGCCTTACA       540

GTTAGAGTAT TCATATTTAC TAACAAGCCA GCTGGAATCT CAGCGAATCT ACTGGGAAAA       600

CAAGATAGTT CGGATAGAGA AGGACACAGC AGAGGAAATT AACAACATGA AGACCAAGTT       660

TAAAGAAACA ATTGAGAAGT GTGATAATCT AGAGCACAAA CTAAATGATC TCCTAAAAGA       720

AAAGCAGTCT GTGGAAAGAA AGTGCACTCA GCTAAACACA AAAGTGGCCA AACTCACCAA       780

CGAGCTCAAA GAGGAGCAGG AAATGAACAA GTGTTTGCGA GCCAACCAAG TCCTCCTGCA       840

GAACAAGCTA AAAGAGGAGG AGAGGGTGCT GAAGGAGACC TGTGACCAAA AAGATCTGCA       900

GATCACCGAG ATCCAGGAGC AGCTGCGTGA CGTCATGTTC TACCTGGAGA CACAGCAGAA       960

AGATCAACCA TCTGCCTGCC GAGACCCGGC AGGAAATCCA GGAGGGACAG ATCAACATCG      1020

CCATGGCCTC GGCCTCGAGC CCTGCCTCTT CGGGGGGCAG TGGGAAGTTG CCCTCCAGGA      1080

AGGGCCGCAG CAAGAGGGGC AAGTGACCTT CAGAGCAACA GACATCCCTG AGACTGTTCT      1140

CCCTGACACT GTGAGAGTGT GCTGGGACCT TCAGCTAAAT GTGAGGGTGG GCCCTAATAA      1200

GTACAAGTGA GGATCAAGCC ACAGTTGTTT GGCTCTTTCA TTTGCTAGTG TGTGATGTAG      1260

TGAATGTAAA GGGTGCTGAC TGGAGAGCTG ATAGAAAGGC GCTGCGTTCG AAAAGGTCTT      1320

AAGAGTTCAC TAACCTCACA TTCTAATGAC CANTTTGCCT TCCTGCTTGG TAGAAGCCCC      1380

ACACTCTGCT GTGCATT                                                    1397
```

(2) INFORMATION FOR SEQ ID NO:18:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (xi) SEQUENCE DESCRIPTION: SEQ ID NO:18:

```
CGGTAATTGA GCANACTTAA AATAAGACCT GTGTTGGAAT TTAGTTTCCT CTGAAGAGGT      60

AGAGGGATAG GTTAGTAAGA TGTATTGTTA AACAACAGGT TTTAGTTTTT GCTTTTATAA     120

TTAGCCACAG GTTTTCAAAT GATCACATTT CAGAATAGGT TTTTAGCCTG TAATTAGGCC     180

TCATCCCCTT TGACCTAAAT GTCTTACATG TTACTTGTTA GCACATCAAC TGTATCACTA     240

ATCACCATCT GNTTTTGTGG GATGTGCTGC AGCATTTCCC AAAAAACTTT ACGTGTAATG     300

TTGCAAAATG AATGTACTCA GACATTCTTA ATTTTTACTT AGGGCAGACC AACTCTTTGA     360

GTCTCTCTTG GACTTATATA TACAGATATC TTAAGAGTGG GAATGTAAAG CATAACCTAA     420

TTCTCTTTCC TATAGAGATT CTATTTTATT TAAAATCTAT TTTTACACTA GTTAGAATCC     480

TGCTGTTTTG GCCAAGTACT TGTCTTGCAT GTCTGACCTT GCAGAAGCTG GGGTGGATCA     540

TAGCATACTA ATGAAGAGAA TTAGAAGTAG TTTACAAAGC TCGCTCACTC CTCATTTCTC     600

TGTGATCCCT TCTATCCAGT GGCCCCACCA CCACCTGGGA AAACAGATTT TTCAGTACAG     660

GTGGGATAAA TGCTCTGAAA GGCTGTGCCC AGAGGAATGA GCAAATAGGC AAGTGTTTCC     720

AAACTACTTG GAGGTTTACA AAAAATATGT CCCAGAAAAA AAAAAAATCT TACCAAGATA     780

CGTAAAAAAA AAAAAAAAA                                                  800
```

(2) INFORMATION FOR SEQ ID NO:19:

(i) SEQUENCE CHARACTERISTICS:
        (A) LENGTH: 1810 base pairs
        (B) TYPE: nucleic acid
        (C) STRANDEDNESS: single
        (D) TOPOLOGY: linear (xi) SEQUENCE DESCRIPTION: SEQ ID NO:19:

```
GCAGCTCCCA GGTGCGTGTT AAAAGCTGGA GGGGGGATAT GTGATCCCAG GACCAAAAGC      60

GCGGGGCCAG ACTCATCGGT TCATTCAACA ACCAGTATTT AGTGCCTGCT GTGTTCTGCA     120

GGCCCTGCCA TAGGCGCTTG ATACAGCGGT GCATAGCGTA TGAAAAGAT CTGTCCTGGC      180

TGAGCATCCG TAATATAAAA ATCTGAAATC TGAAATGCTC CAAAATCCTA AACTTTTTGA     240

GTGCTGACAT TATGCCACAA ATGGAAAATT TCATACCTGA CCTTATGTGG GTTGCANTCA     300

AAACACAGGT GCACAACACC CAGTTCATGC AACATCCCCA ATGGGAAAAA AGACCCCCCC     360

AGCTCTCTTC TGCTGCAGTT TTTCTGCTCA CACCTGGATT TCCCCATGCA TTCCCACAAA     420

AAGTAATTAA ATGGCATGCG TGCAGGCTGG ACACGCCAAC AACAGGTTTC CCACAATGCC     480

CCACATGGGG CCAAGACCTG TGTGCATTAC TCATTGCATT TTTTTGCTTA TTCTCTGCTG     540

TGTGGTATAA ATATATTGTT GAAAATGTCA AAAAGACCTA AGATACCCC TGTGAATATC      600

AGTGATAAGA AAAAGAGGAA GCATTTATGT TTATCTATAG CACAGAAAGT CAAGTTGTTG     660

GAGAAACTGG ACAGTGGTGT AAGTGTGAAA CATCTTACAG AAGAGTATGG TGTTGGAATG     720

ACCACCATAT ATGACCTGAA GAAACAGAAG GATAAACTGT TGAAGTTTTA TGCTGAAAGT     780

GATGAGCAGA TATTAATGAA AAATAGAAAA ACACTTCATA AAGCTAAAAA TGAAGATCTT     840
```

-continued

```
GATCGTGTAT TGAAAGAGTG GATCCGTCAG CGTCGCAGTG AACACATGCC ACTTAATGGT      900

ATGCTGATCA TGAAACAAGC AAAGATATAT CACAATGAAC TAAAAATTGA GGGGAACTGT      960

GAATATTCAA CAGGCTGGTT GCAGAAATTT AAGAAAAGAC ATGGCATTAA ATTTTTAAAG     1020

ACTTGTGGCA ATAAAGCATC TGCTGGTCAT GAAGCAACAG AGAAGTTTAC TGGCAATTTC     1080

AGTAATGATG ATGAACAAGA TGGTAACTTT GAAGGATTCA NTATGTCAAG TGAGAAAAAA     1140

ATAATGTCTG ACCTCCTTAC ATATACAAAA AATATACATC CAGAGACTGT CAGTAAGCTG     1200

GAAGAAGAGG ATATCTTTNA TGTTTTTAAC AGTAATAATG AGGCTCCAGT TGTTCATTCA     1260

TTGTCCAATG GTGAAGTAAC AAAAATGGTT CTGAATCAAG ATGATCATGA TGATAATGAT     1320

AATGAAGATG ATGTTAACAC TGCAGAAAAA GTGCCTATAG ACGACATGGT AAAAATGTGT     1380

GATGGGCTTA TTAAAGGACT AGAGCAGCAT GCATTCATAA CAGAGCAAGA ATCATGTCA      1440

GTTTATAAAA TCAAGAGAG ACTTCTAAGA CAAAAAGCAT CATTAATGAG GCAGATGACT      1500

CTGAAAGAAA CATTTAAAAA AGCCATCCAG AGGAATGCTT CTTCCTCTCT ACAGGACCCA     1560

CTTCTTGGTC CCTCAACTGC TTCTGATGCT TCTTCTCACC TAAAAATAAA ATAAAATACA     1620

GTGTACAGTA ACCTTTTAGT CAAAACAGCA TCATACTTGG AAACTGAAAG CCTACTGTTA     1680

TTTGTTATTG TTGCTTAACA GCTGATACAG GTATTCTGGT GACACTACTG TGCTGGCTTA     1740

CTTAACCTGA ATACACTATT TTTTTCGTTG TAAAAAAAAA AAAAAAANAA NAAAAAAAA      1800

AAAAAANANA                                                            1810
```

(2) INFORMATION FOR SEQ ID NO:20:

(i) SEQUENCE CHARACTERISTICS:
        (A) LENGTH: 70 amino acids
        (B) TYPE: amino acid
        (C) STRANDEDNESS:
        (D) TOPOLOGY: linear (xi) SEQUENCE DESCRIPTION: SEQ ID NO:20:

```
Ala Arg Glu Gly Gly Lys Met Val Leu Glu Ser Thr Met Val Cys Val
1               5                  10                  15

Asp Asn Ser Glu Tyr Met Arg Asn Gly Asp Phe Leu Pro Thr Arg Leu
            20                  25                  30

Gln Ala Gln Gln Asp Ala Val Asn Ile Xaa Cys His Ser Lys Thr Arg
        35                  40                  45

Ser Asn Pro Glu Asn Asn Val Gly Leu Ile Thr Leu Ala Asn Asp Cys
    50                  55                  60

Glu Val Leu Thr Thr Leu
65              70
```

(2) INFORMATION FOR SEQ ID NO:21:

(i) SEQUENCE CHARACTERISTICS:
        (A) LENGTH: 100 amino acids
        (B) TYPE: amino acid
        (C) STRANDEDNESS:
        (D) TOPOLOGY: linear (xi) SEQUENCE DESCRIPTION: SEQ ID NO:21:

```
Ala Arg Glu Ser Thr Met Val Cys Val Asp Asn Ser Glu Tyr Met Arg
1               5                  10                  15

Asn Gly Asp Phe Leu Pro Thr Arg Leu Gln Ala Gln Gln Asp Ala Val
            20                  25                  30

Asn Ile Val Cys His Ser Lys Thr Arg Ser Asn Pro Glu Asn Asn Val
        35                  40                  45
```

Gly Leu Ile Thr Leu Ala Asn Asp Cys Glu Val Leu Thr Thr Leu Thr
    50                  55                  60

Pro Asp Thr Gly Arg Ile Leu Ser Lys Leu His Thr Val Gln Pro Lys
 65              70                  75                  80

Gly Lys Ile Thr Phe Cys Thr Gly Ile Arg Val Ala His Leu Ala Leu
                85                  90                  95

Lys His Arg Gln
            100

(2) INFORMATION FOR SEQ ID NO:22:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (xi) SEQUENCE DESCRIPTION: SEQ ID NO:22:

CGGCACGAGA AGGTGGCAAG ATGGTGTTGG AAAGCACTAT GGTGTGTGTG GACAACAGTG        60

AGTATATGCG GAATGGAGAC TTCTTACCCA CCAGGCTGCA GGCCCAGCAG GATGCTGTCA       120

ACATANTTTG TCATTCAAAG ACCCGCAGCA ACCCTGAGAA CAACGTGGGC CTTATCACAC       180

TGGCTAATGA CTGTGAAGTG CTGACCACAC TCAC                                  214

(2) INFORMATION FOR SEQ ID NO:23:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (xi) SEQUENCE DESCRIPTION: SEQ ID NO:23:

TATGGACACA TTTGAGCCAG CCAAGGAGGA GGATGATTAC GACGTGATGC AGGACCCCGA        60

GTTCCTTCAG AGTGTCCTAG AGAACCTCCC AGGTGTGGAT CCCAACAATG AAGCCATTCG       120

AAATGNTATG GGCTCCCTGG CCTCCCAGGC CACCAAGGAC GGCAAGAAGG ACAAGAAGGA       180

GGAAGACAAG AAGTGAGACT GGAGGGAAAG GGTAGCTGAG TCTGCTTAGG GGACTGCATG       240

GGAAGCACGG AATATAGGGT TAGATGTGTG TTATCTGTAA CCATTACAGC CTAAATAAAG       300

CTTGGCAACT TTTTAAAAAA AAAAAAAAAA AAAAAAAAAA AAAAAAAAAA AAAAAAAAAA       360

AAAAAAAAAC TCGAG                                                       375

(2) INFORMATION FOR SEQ ID NO:24:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (xi) SEQUENCE DESCRIPTION: SEQ ID NO:24:

CGGCACGAGA AAGCACTATG GTGTGTGTGG ACAACAGTGA GTATATGCGG AATGGAGACT        60

TCTTACCCAC CAGGCTGCAG GCCCAGCAGG ATGCTGTCAA CATAGTTTGT CATTCAAAGA       120

CCCGCAGCAA CCCTGAGAAC AACGTGGGCC TTATCACACT GGCTAATGAC TGTGAAGTGC       180

TGACCACACT CACCCCAGAC ACTGGCCGTA TCCTGTCCAA GCTACATACT GTCCAACCCA       240

AGGGCAAGAT CACCTTCTGC ACGGGCATCC GCGTTGCCCA TCTGGCTCTG AAGCACCGAC       300

AAGG                                                                   304

(2) INFORMATION FOR SEQ ID NO:25:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:25:

```
Val Arg Gly Gly Gly Gly Gly Pro Gly Gly Gly Val Gly Gly
 1               5                  10                  15

Arg Cys Gly Gly Gly Gly
            20
```

(2) INFORMATION FOR SEQ ID NO:26:

(i) SEQUENCE CHARACTERISTICS:
        (A) LENGTH: 78 amino acids
        (B) TYPE: amino acid
        (C) STRANDEDNESS:
        (D) TOPOLOGY: linear (xi) SEQUENCE DESCRIPTION: SEQ ID NO:26:

```
Ala Arg Ala Ala Arg Ala Lys Ala Gln Ala Leu Ile Gln Asn Leu Ser
 1               5                  10                  15

Leu Leu Leu Val Asp Ala Ser Val Gly Thr Ile Gln Cys Leu Glu Glu
                20                  25                  30

Ile Leu Cys Glu Phe Val Gln Lys Asp Glu Leu Lys Pro Ala Val Thr
            35                  40                  45

Xaa Leu Leu Trp Glu Arg Ala Thr Glu Lys Val Ala Cys Cys Pro Leu
    50                  55                  60

Glu Arg Cys Ser Ser Val Met Leu Leu Gly Met Met Ala Arg
65                  70                  75
```

(2) INFORMATION FOR SEQ ID NO:27:

(i) SEQUENCE CHARACTERISTICS:
        (A) LENGTH: 384 amino acids
        (B) TYPE: amino acid
        (C) STRANDEDNESS:
        (D) TOPOLOGY: linear (xi) SEQUENCE DESCRIPTION: SEQ ID NO:27:

```
Lys Met Val Leu Glu Ser Thr Met Val Cys Val Asp Asn Ser Glu Tyr
 1               5                  10                  15

Met Arg Asn Gly Asp Phe Leu Pro Thr Arg Leu Gln Ala Gln Gln Asp
                20                  25                  30

Ala Val Asn Ile Val Cys His Ser Lys Thr Arg Ser Asn Pro Glu Asn
            35                  40                  45

Asn Val Gly Leu Ile Thr Leu Ala Asn Asp Cys Glu Val Leu Thr Thr
    50                  55                  60

Leu Thr Pro Asp Thr Gly Arg Ile Leu Ser Lys Leu His Thr Val Gln
65                  70                  75                  80

Pro Lys Gly Lys Ile Thr Phe Cys Thr Gly Ile Arg Val Ala His Leu
                85                  90                  95

Ala Leu Lys His Arg Gln Gly Lys Asn His Lys Met Arg Ile Ile Ala
            100                 105                 110

Phe Val Gly Ser Pro Val Glu Asp Asn Glu Lys Asp Leu Val Lys Leu
        115                 120                 125
```

-continued

```
Ala Lys Arg Leu Lys Lys Glu Lys Val Asn Val Asp Ile Ile Asn Phe
    130                 135                 140

Gly Glu Glu Val Asn Thr Glu Lys Leu Thr Ala Phe Val Asn Thr
145                 150                 155                 160

Leu Asn Gly Lys Asp Gly Thr Gly Ser His Leu Val Thr Val Pro Pro
                165                 170                 175

Gly Pro Ser Leu Ala Asp Ala Leu Ile Ser Ser Pro Ile Leu Ala Gly
            180                 185                 190

Glu Gly Gly Ala Met Leu Gly Leu Gly Ala Ser Asp Phe Glu Phe Gly
        195                 200                 205

Val Asp Pro Ser Ala Asp Pro Glu Leu Ala Leu Ala Leu Arg Val Ser
    210                 215                 220

Met Glu Glu Gln Arg Gln Arg Gln Glu Glu Ala Arg Arg Ala Ala
225                 230                 235                 240

Ala Ala Ser Ala Ala Glu Ala Gly Ile Ala Thr Thr Gly Thr Glu Asp
                245                 250                 255

Ser Asp Asp Ala Leu Leu Lys Met Thr Ile Ser Gln Gln Glu Phe Gly
                260                 265                 270

Arg Thr Gly Leu Pro Asp Leu Ser Ser Met Thr Glu Glu Glu Gln Ile
            275                 280                 285

Ala Tyr Ala Met Gln Met Ser Leu Gln Gly Ala Glu Phe Gly Gln Ala
    290                 295                 300

Glu Ser Ala Asp Ile Asp Ala Ser Ser Ala Met Asp Thr Ser Glu Pro
305                 310                 315                 320

Ala Lys Glu Glu Asp Asp Tyr Asp Val Met Gln Asp Pro Glu Phe Leu
                325                 330                 335

Gln Ser Val Leu Glu Asn Leu Pro Gly Val Asp Pro Asn Asn Glu Ala
                340                 345                 350

Ile Arg Asn Ala Met Gly Ser Leu Pro Pro Arg Pro Arg Thr Ala
            355                 360                 365

Arg Arg Thr Arg Arg Arg Lys Thr Arg Ser Glu Thr Gly Gly Lys Gly
370                 375                 380
```

(2) INFORMATION FOR SEQ ID NO:28:

(i) SEQUENCE CHARACTERISTICS:
        (A) LENGTH: 68 amino acids
        (B) TYPE: amino acid
        (C) STRANDEDNESS:
        (D) TOPOLOGY: linear (xi) SEQUENCE DESCRIPTION: SEQ ID NO:28:

```
Ala Arg Asp Ala Tyr Ser Phe Ser Arg Lys Ile Thr Glu Ala Ile Gly
1               5                   10                  15

Ile Ile Ser Lys Met Met Tyr Glu Asn Thr Thr Thr Val Val Gln Glu
            20                  25                  30

Val Ile Glu Phe Phe Val Met Val Phe Gln Phe Gly Val Pro Gln Ala
        35                  40                  45

Leu Phe Gly Val Arg Arg Met Leu Pro Leu Ile Trp Ser Lys Glu Pro
    50                  55                  60

Gly Val Arg Glu
65
```

(2) INFORMATION FOR SEQ ID NO:29:

(i) SEQUENCE CHARACTERISTICS:
        (A) LENGTH: 97 amino acids (B) TYPE: amino acid
                    (C) STRANDEDNESS:
                    (D) TOPOLOGY: linear (xi) SEQUENCE DESCRIPTION: SEQ ID NO:29:

Ala Arg Ala Gln Ala Leu Phe Gly Val Arg Arg Met Leu Pro Leu Ile
1               5                   10                  15

Trp Ser Lys Glu Pro Gly Val Arg Glu Ala Val Leu Asn Ala Tyr Arg
            20                  25                  30

Gln Leu Tyr Leu Asn Pro Lys Gly Asp Ser Ala Arg Ala Lys Ala Gln
        35                  40                  45

Ala Leu Ile Gln Asn Leu Ser Leu Leu Val Asp Ala Ser Val Gly
50                  55                  60

Thr Ile Gln Cys Leu Glu Ile Leu Cys Glu Phe Val Gln Lys Asp
65                  70                  75                  80

Glu Leu Lys Pro Ala Val Thr Gln Leu Leu Trp Glu Pro Ala Thr Glu
            85                  90                  95

Lys (2) INFORMATION FOR SEQ ID NO:30:

(i) SEQUENCE CHARACTERISTICS:
            (A) LENGTH: 116 amino acids
            (B) TYPE: amino acid
            (C) STRANDEDNESS:
            (D) TOPOLOGY: linear (xi) SEQUENCE DESCRIPTION: SEQ ID NO:30:

Ala Arg Ala Thr Thr Ala Phe Gly Cys Arg Ile Trp Asn Pro Cys Ala
1               5                   10                  15

Ala Leu Thr Met Lys Gln Ser Ser Asn Val Pro Ala Phe Leu Ser Lys
            20                  25                  30

Leu Trp Thr Leu Val Glu Glu Thr His Thr Asn Glu Phe Ile Thr Trp
        35                  40                  45

Ser Gln Asn Gly Gln Ser Phe Leu Val Leu Asp Glu Gln Arg Phe Ala
    50                  55                  60

Lys Glu Ile Leu Pro Lys Tyr Phe Lys His Asn Asn Met Ala Ser Phe
65                  70                  75                  80

Val Arg Gln Leu Asn Met Tyr Gly Phe Arg Lys Val Ile His Ile Asp
            85                  90                  95

Ser Gly Ile Val Lys Gln Glu Arg Asp Gly Pro Val Glu Phe Gln His
                100                 105                 110

Pro Tyr Phe Gln
            115

(2) INFORMATION FOR SEQ ID NO:31:

(i) SEQUENCE CHARACTERISTICS:
            (A) LENGTH: 124 amino acids
            (B) TYPE: amino acid
            (C) STRANDEDNESS:
            (D) TOPOLOGY: linear (xi) SEQUENCE DESCRIPTION: SEQ ID NO:31:

Ala Arg Gly Ala Thr Cys Glu Arg Cys Lys Gly Phe Ala Pro Ala
1               5                   10                  15

Glu Lys Ile Val Asn Ser Asn Gly Glu Leu Tyr His Glu Gln Cys Phe
            20                  25                  30

Val Cys Ala Gln Cys Phe Gln Gln Phe Pro Glu Gly Leu Phe Tyr Glu

```
            35                  40                  45
Phe Glu Gly Arg Lys Tyr Cys Glu His Asp Phe Gln Met Leu Phe Ala
         50                  55                  60

Pro Cys Cys His Gln Cys Gly Glu Phe Ile Ile Gly Arg Val Ile Lys
 65                  70                  75                  80

Ala Met Asn Asn Ser Trp His Pro Glu Cys Phe Arg Cys Asp Leu Cys
                 85                  90                  95

Gln Glu Val Leu Ala Asp Ile Gly Phe Val Lys Asn Ala Gly Arg His
             100                 105                 110

Leu Cys Arg Pro Cys His Asn Arg Glu Lys Ala Arg
             115                 120
```

(2) INFORMATION FOR SEQ ID NO:32:

(i) SEQUENCE CHARACTERISTICS:
        (A) LENGTH: 768 base pairs
        (B) TYPE: nucleic acid
        (C) STRANDEDNESS: single
        (D) TOPOLOGY: linear (xi) SEQUENCE DESCRIPTION: SEQ ID NO:32:

```
TACGAGGAGG AGGAGGAGGA GGCCCCGGAG GAGGAGGCGT TGGAGGTCGA TGCGGAGGCG     60
GAGGATGAGG AGGCCGAGGC GCCGGAGGAG GCCGAGGCGC CGGAGCAGGA GGAGGCCGGC    120
CGGAGGCGGC ATGAGACGAG CGTGGCGGCC GCGGCTGCTC GGGGCCGCGC TGGTTGCCCA    180
TTGACAGCGG CGTCTGCAGC TCGCTTCAAG ATGGCCGCTT GGCTCGCATT CATTTTCTGC    240
TGAACGACTT TTAACTTTCA TTGTCTTTTC CGCCCGCTTC GATCGCCTCG CGCCGGCTGC    300
TCTTTCCGGG ATTTTTTATC AAGCAGAAAT GCATCGAACA ACGAGAATCA AGATCACTGA    360
GCTAAATCCC CACCTGATGT GTGTGCTTTG TGGAGGGTAC TTCATTGATG CCACAACCAT    420
AATAGAATGT CTACATTCCT TCTGTAAAAC GTGTATTGTT CGTTACCTGG AGACCAGCAA    480
GTATTGTCCT ATTTGTGATG TCCAAGTTCA AAGACCAGA CCACTACTGA ATATAAGGTC     540
AGATAAAACT CTCCAAGATA TTGTATACAA ATTAGTTCCA GGGCTTTTCA AAATGAAAT     600
GAAGAGAAGA AGGGATTTTT ATGCAGCTCA TCCTTCTGCT GATGCTGCCA ATGGCTCTAA    660
TGAAGATNGA GGAGAGGTTG CAGATGAAGA TAAGAGAATT ATAACTGATG ATGAGATAAT    720
AAGCTTATCC ATTGAATTCT TGACCAGAA CAGATTGGAT CGGAAAGT                  768
```

(2) INFORMATION FOR SEQ ID NO:33:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (xi) SEQUENCE DESCRIPTION: SEQ ID NO:33:

```
TTTAAATAAA CCAGCAGGTT GCTAAAAGAA GGCATTTTAT CTAAAGTTAT TTAATAGGT      60
GGTATAGCAG TAATTTTAAA TTTAAGAGTT GCTTTTACAG TTAACAATGG AATATGCCTT    120
CTCTGCTATG TCTGAAAATA GAAGNTATTT ATTATGAGCT TNTACAGGTA TTTTTAAATA    180
GAGCAAGCAT GTTGAATTTA AAATATGAAT AACCCCACCC AACAATTTTC AGTTTATTTT    240
TTGCTTTGGT CGAACTTGGT GTGTGTTCAT CACCCATCAG TTATTTGTGA GGGTGTTTAT    300
TCTATATGAA TATTGTTTCA TGTTTGTATG GGAAAATTGT AGCTAAACAT TTCATTGTCC    360
CCAGTCTGCA AAAGAAGCAC AATTCTATTG CTTTGTCTTG CTTATAGTCA TTAAATCATT    420
```

```
ACTTTTACAT ATATTGCTGT TACTTCTGCT TTCTTTAAAA ATATAGTAAA GGATGTTTTA      480

TGAAGTCACA AGATACATAT ATTTTTATTT TGACCTAAAT TTGTACAGTC CCATTGTAAG      540

TGTTGTTTCT AATTATAGAT GTAAAATGAA ATTTCATTTG TAATTGGAAA AAATCCAATA      600

AAAAGGATAT TCATTTAAAA AAAAAAAAAA AAAAAAAAAA AA                         642

(2) INFORMATION FOR SEQ ID NO:34:

(i) SEQUENCE CHARACTERISTICS:
         (A) LENGTH: 236 base pairs
         (B) TYPE: nucleic acid
         (C) STRANDEDNESS: single
         (D) TOPOLOGY: linear (xi) SEQUENCE DESCRIPTION: SEQ ID NO:34:

CGGCACGAGC TGCCAGAGCC AAGGCCCAGG CTTTGATTCA GAATCTCTCT CTGCTGCTAG       60

TGGATGCCTC GGTTGGGACC ATTCAGTGTC TTGAGGAAAT TCTCTGTGAG TTTGTGCAGA      120

AGGATGAGTT GAAACCAGCA GTGACCCANC TGCTGTGGGA GCGGGCCACC GAGAAAGTCG      180

CCTGCTGTCC TCTGGAACGC TGTTCCTCTG TCATGCTTCT TGGCATGATG GCACGA         236

(2) INFORMATION FOR SEQ ID NO:35:

(i) SEQUENCE CHARACTERISTICS:
         (A) LENGTH: 333 base pairs
         (B) TYPE: nucleic acid
         (C) STRANDEDNESS: single
         (D) TOPOLOGY: linear (xi) SEQUENCE DESCRIPTION: SEQ ID NO:35:

CCGGGCGTAT TGGCGTGCGC CTGTAATCCC AGCTAACTCA AGAGGCTGAG GCAGGAGAAT       60

CGCCTGAACC CAGAGGCGGA GGTTGTAGTG AGCCGAAATC ACACCATTGC ACTCCAGCTT      120

GGGCAACAAT AGCGAACCTC CATCTCAAAT TAAAAAAAAA AATGCCTACA CGCTCTTTAA      180

AATGCAAGGC TTTCTCTTAA ATTAGCCTAA CTGAACTGCG TTGAGCTGCT TCAACTTTGG      240

AATATATGTT TGCCAATCTC CTTGTTTTCT AATGAATAAA TGTTTTTATA TACTTTTAGA      300

AAAAAAAAAA AAAAAAAAAA AAAAAACTC GAG                                    333

(2) INFORMATION FOR SEQ ID NO:36:

(i) SEQUENCE CHARACTERISTICS:
         (A) LENGTH: 1272 base pairs
         (B) TYPE: nucleic acid
         (C) STRANDEDNESS: single
         (D) TOPOLOGY: linear (xi) SEQUENCE DESCRIPTION: SEQ ID NO:36:

GCAAGATGGT GTTGGAAAGC ACTATGGTGT GTGTGGACAA CAGTGAGTAT ATGCGGAATG       60

GAGACTTCTT ACCCACCAGG CTGCAGGCCC AGCAGGATGC TGTCAACATA GTTTGTCATT      120

CAAAGACCCG CAGCAACCCT GAGAACAACG TGGGCCTTAT CACACTGGCT AATGACTGTG      180

AAGTGCTGAC CACACTCACC CCAGACACTG GCCGTATCCT GTCCAAGCTA CATACTGTCC      240

AACCCAAGGG CAAGATCACC TTCTGCACGG GCATCCGCGT GGCCCATCTG GCTCTGAAGC      300

ACCGACAAGG CAAGAATCAC AAGATGCGCA TCATTGCCTT TGTGGGAAGC CCAGTGGAGG      360

ACAATGAGAA GGATCTGGTG AAACTGGCTA AACGCCTCAA GAAGGAGAAA GTAAATGTTG      420

ACATTATCAA TTTTGGGGAA GAGGAGGTGA ACACAGAAAA GCTGACAGCC TTTGTAAACA      480

CGTTGAATGG CAAAGATGGA ACCGGTTCTC ATCTGGTGAC AGTGCCTCCT GGGCCCAGTT      540
```

```
TGGCTGATGC TCTCATCAGT TCTCCGATTT TGGCTGGTGA AGGTGGTGCC ATGCTGGGTC     600

TTGGTGCCAG TGACTTTGAA TTTGGAGTAG ATCCCAGTGC TGATCCTGAG CTGGCCTTGG     660

CCCTTCGTGT ATCTATGGAA GAGCAGCGGC AGCGGCAGGA GGAGGAGGCC CGGCGGGCAG     720

CTGCAGCTTC TGCTGCTGAG GCCGGGATTG CTACGACTGG GACTGAAGAC TCAGACGATG     780

CCCTGCTGAA GATGACCATC AGCCAGCAAG AGTTTGGCCG CACTGGGCTT CCTGACCTAA     840

GCAGTATGAC TGAGGAAGAG CAGATTGCTT ATGCCATGCA GATGTCCCTG CAGGGAGCAG     900

AGTTTGGCCA GGCGGAATCA GCAGACATTG ATGCCAGCTC AGCTATGGAC ACATCTGAGC     960

CAGCCAAGGA GGAGGATGAT TACGACGTGA TGCAGGACCC CGAGTTCCTT CAGAGTGTCC    1020

TAGAGAACCT CCCAGGTGTG GATCCCAACA ATGAAGCCAT TCGAAATGCT ATGGGCTCCC    1080

TGCCTCCCAG GCCACCAAGG ACGGCAAGAA GGACAAGAAG GAGGAAGACA AGAAGTGAGA    1140

CTGGAGGGAA AGGGTAGCTG AGTCTGCTTA GGGGACTGCA TGGAAGCAC GGAATATAGG     1200

GTTAGATGTG TGTTATCTGT AACCATTACA GCCTAAATAA AGCTTGGCAA CTTTTAAAAA    1260

AAAAAAAAAA AA                                                       1272

(2) INFORMATION FOR SEQ ID NO:37:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (xi) SEQUENCE DESCRIPTION: SEQ ID NO:37:

CGGCACGAGA TGCCTACAGC TTCTCCCGGA AGATTACAGA GGCCATTGGC ATCATCAGCA      60

AGATGATGTA TGAAAACACA ACTACAGTGG TGCAGGAGGT GATTGAATTC TTTGTGATGG     120

TCTTCCAATT TGGGGTACCC CAGGCCCTGT TTGGGGTGCG CCGTATGCTG CCTCTCATCT     180

GGTCTAAGGA GCCTGGTGTC CGGGAA                                         206

(2) INFORMATION FOR SEQ ID NO:38:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (xi) SEQUENCE DESCRIPTION: SEQ ID NO:38:

TACTAAAAAT AAAAAATTAG CCGGGCGTAT TGGCGTGCGC CTGTAATCCC AGCTACTCAA      60

GAGGCTGAGG CAGGAGAATC GCCTGAACCC AGAGGCGGAG GTTGTAGTGA GCCGAAATCA     120

CACCATTGCA CTCCAGCTTG GCAACAATA GCGAACCTCC ATCTCAAATT AAAAAAAAAA      180

TGCCTACACG CTCTTTAAAA TGCAAGGCTT TCTCTTAAAT TAGCCTAACT GAACTGCGTT     240

GAGCTGCTTC AACTTTGGAA TATATGTTTG CCAATCTCCT TGTTTTCTAA TGAATAAATG     300

TTTTTATATA CTTTTAAGA GAGAAAAAAA ANAAACTCGA G                          341

(2) INFORMATION FOR SEQ ID NO:39:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (xi) SEQUENCE DESCRIPTION: SEQ ID NO:39:
```

```
CGGCACGAGC CCAGGCCCTG TTTGGGGTGC GCCGTATGCT GCCTCTCATC TGGTCTAAGG        60

AGCCTGGTGT CCGGGAAGCC GTGCTTAATG CCTACCGCCA ACTCTACCTC AACCCCAAAG       120

GGGACTCTGC CAGAGCCAAG GCCCAGGCTT TGATTCAGAA TCTCTCTCTG CTGCTAGTGG       180

ATGCCTCGGT TGGGACCATT CAGTGTCTTG AGGAAATTCT CTGTGAGTTT GTGCAGAAGG       240

ATGAGTTGAA ACCAGCAGTG ACCCAGCTGC TGTGGGAACC GGCCACCGAG AAA             293

(2) INFORMATION FOR SEQ ID NO:40:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (xi) SEQUENCE DESCRIPTION: SEQ ID NO:40:

CGGCACGAGC TACCACCGCG TTCGGGTGTA GAATTTGGAA TCCCTGCGCC GCGTTAACAA        60

TGAAGCAGAG TTCGAACGTG CCGGCTTTCC TCAGCAAGCT GTGGACGCTT GTGGAGGAAA      120

CCCACACTAA CGAGTTCATC ACCTGGAGCC AGAATGGCCA AAGTTTTCTG GTCTTGGATG      180

AGCAACGATT TGCAAAAGAA ATTCTTCCCA AATATTTCAA GCACAATAAT ATGGCAAGCT      240

TTGTGAGGCA ACTGAATATG TATGGTTTCC GTAAAGTAAT ACATATCGAC TCTGGAATTG      300

TTAAGCAAGA AAGAGATGGT CCTGTAGAAT TCAGCATCC TTACTTCCAA                  350

(2) INFORMATION FOR SEQ ID NO:41:

(i) SEQUENCE CHARACTERISTICS:
        (A) LENGTH: 377 base pairs
        (B) TYPE: nucleic acid
        (C) STRANDEDNESS: single
        (D) TOPOLOGY: linear (xi) SEQUENCE DESCRIPTION: SEQ ID NO:41:

TCCTAAAGCT TTCTCTGCTC CAGTTATTTT TATTAAATAT TTTTCACTTG GCTTATTTTT        60

AAAACTGGGA ACATAAAGTG CCTGTATCTT GTAAAACTTC ATTTGTTTCT TTTGGTTCAG      120

AGAAGTTCAT TTATGTTCAA AGACGTTTAT TCATGTTCAA CAGGAAAGAC AAAGTGTACG      180

TGAATGCTCG CTGTCTGATA GGGTTCCAGC TCCATATATA TAGAAAGATC GGGGGTGGGA      240

TGGGATGGAG TGAGCCCCAT CCAGTTAGTT GGACTAGTTT TAAATAAAGG TTTTCCGGTT      300

TGTGTTTTTT TGAACCATAC TGTTTAGTAA AATAAATACA ATGAATGTTG NAAAAAAAA       360

AAAAAAAAAA ACTCGAG                                                    377

(2) INFORMATION FOR SEQ ID NO:42:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (xi) SEQUENCE DESCRIPTION: SEQ ID NO:42:

CGGCACGAGG CGCCACTTGC GAGCGCTGCA AGGGCGGCTT TGCGCCCGCT GAGAAGATCG        60

TGAACAGTAA TGGGGAGCTG TACCATGAGC AGTGTTTCGT GTGCGCTCAG TGCTTCCAGC      120

AGTTCCCAGA AGGACTCTTC TATGAGTTTG AAGGAAGAAA GTACTGTGAA CATGACTTTC      180

AGATGCTCTT TGCCCCTTGC TGTCATCAGT GTGGTGAATT CATCATTGGC CGAGTTATCA      240

AAGCCATGAA TAACAGCTGG CATCCGGAGT GCTTCCGCTG TGACCTCTGC CAGGAAGTTC      300
```

```
TGGCAGATAT CGGGTTTGTC AAGAATGCTG GGAGACACCT GTGTCGCCCC TGTCATAATC      360

GTGAGAAAGC CAGA                                                        374
```

(2) INFORMATION FOR SEQ ID NO:43:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (xi) SEQUENCE DESCRIPTION: SEQ ID NO:43:

```
CTTTGCATTT TACAGTAAGA ATCAAAGTCC CTTCAGTGTG CCTTTGTCAG CTAATATGTG       60

ACCAGCAATG ACAACCTTGG GAGTATTTAT TAAATATTAT GCTATGAATA TAGGCAACAC      120

AGAACAGGGT TTGCAGTATA GCGTCTTGAT GCTAAATTCT CATATACCTC TACACGAGAA      180

ATATGGAGGA GAAAACAAG CATTTACATA TATTCTTCGT CACTTTGAAG ATGCATGACC       240

TGAACTCGAC TGCTTGTGTT TGTTTACATA TCAGGCATAC CCAGGCATCT CCTGCAGCCA      300

GAGGTTCCAT TGCTGTCTTT GCTCAGTCCT CTTTTAAAAT ATGAATTAGT GGACAGGCAC      360

GGTGCCTCAC ACCTGTAATC CCAGCACTTT GGGAGGTCGA GGCAGGTGGA TCACGAGGTC      420

AGGAGATCAA GACCATCCTG GCTACCACTG AAACCCCATC TCTACTACAA AAAAAAAAA      480

AAAAAACTCG AG                                                         492
```

(2) INFORMATION FOR SEQ ID NO:44:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:44:

```
Ser Gln Ile Cys Glu Leu Val Ala His Glu Thr Ile Ser Phe Leu
1               5                   10                  15
```

(2) INFORMATION FOR SEQ ID NO:45:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:45:

```
Xaa Xaa Xaa Xaa Xaa Ser Ile Leu Asp Glu Val Ile Arg Gly Thr
1               5                   10                  15
```

(2) INFORMATION FOR SEQ ID NO:46:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:46:

```
Val Val Lys Thr Tyr Leu Ile Ser Ser Ile Pro Gln Gly Ala Phe Asn
1               5                   10                  15

Tyr Lys Tyr Thr Ala
            20
```

(2) INFORMATION FOR SEQ ID NO:47:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:47:

Val Val Lys Thr Tyr Leu Ile Ser Ser Ile Pro Leu Gln Ala Phe Asn
1               5                  10                  15

Tyr Lys Tyr Thr Ala
            20

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:48:

Xaa Ala Lys Lys Phe Leu Asp Ala Glu His Lys Leu Asn Phe Ala
1               5                  10                  15

(2) INFORMATION FOR SEQ ID NO:49:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:49:

Xaa Xaa Xaa Lys Ile Lys Lys Phe Ile Gln Glu Asn Ile Phe Gly
1               5                  10                  15

(2) INFORMATION FOR SEQ ID NO:50:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:50:

Xaa Lys Val Lys Val Gly Val Asn Gly Phe Gly Arg Ile Gly Arg Leu
1               5                  10                  15

Val Thr (2) INFORMATION FOR SEQ ID NO:51:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:51:

Xaa Tyr Gln Tyr Pro Ala Leu Thr Xaa Glu Gln Lys Lys Glu Leu
1               5                  10                  15

(2) INFORMATION FOR SEQ ID NO:52:

(i) SEQUENCE CHARACTERISTICS:
        (A) LENGTH: 14 amino acids

```
        (B) TYPE: amino acid
        (C) STRANDEDNESS: single
        (D) TOPOLOGY: linear (xi) SEQUENCE DESCRIPTION: SEQ ID NO:52:

Xaa Pro Ala Val Tyr Phe Lys Xaa Xaa Phe Leu Asp Xaa Asp
1               5                   10

(2) INFORMATION FOR SEQ ID NO:53:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:53:

Xaa Pro Ala Val Tyr Phe Lys Glu Gln Phe Leu Asp Gly Asp Gly
1               5                   10                  15

(2) INFORMATION FOR SEQ ID NO:54:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:54:

Xaa Xaa Val Ala Val Leu Xaa Ala Ser Xaa Xaa Ile Gly Gln Pro Leu
1               5                   10                  15

Ser Leu (2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:55:

Val Val Lys Thr Tyr Leu Ile Ser Xaa Ile Pro Leu Gln Gly Ala
1               5                   10                  15

(2) INFORMATION FOR SEQ ID NO:56:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:56:

Xaa Xaa Lys Thr Tyr Leu Ile Ser Ser Ile Pro Leu Gln Gly Ala
1               5                   10                  15

(2) INFORMATION FOR SEQ ID NO:57:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:57:

Met Asp Ile Pro Gln Thr Lys Gln Asp Leu Glu Leu Pro Lys Leu
```

(2) INFORMATION FOR SEQ ID NO:58:

(i) SEQUENCE CHARACTERISTICS:
        (A) LENGTH: 1497 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:58:

```
GGAGGGCAGA GATATCCAGT AGACAGAAGA TCTTGGACCC CAGGAAGTAT ATTGGAAGAG    60
GTGCCTGGAG AAATGGATGC TAGAAGAAAA CACTGGAAGG AGAATATGTT TACTCCTTTT   120
TTTAGTGCAC AAGATGTTCT AGAAGAGACT TCTGAGCCTG AATCTTCTTC TGAACAAACG   180
ACTGCAGATA GCAGCAAGGG AATGGAAGAA ATTTATAATT TGTCCAGTAG AAAGTTTCAG   240
GAAGAAAGTA AATTTAAGAG GAAAAATAT ATTTTCCAAC TAAATGAAAT AGAACAAGAA   300
CAAAATTTAA GAGAGAACAA GAGAAACATT TCAAAGAATG AAACAGACAC AAATTCTGCA   360
TCCTATGAAT CATCTAATGT GGATGTTACA ACAGAAGAAA GCTTTAACAG CACAGAAGAT   420
AACTCTACCT GCAGTACAGA TAACTTACCA GCTCTACTAA GACAAGACAT AAGAAAGAAA   480
TTTATGGAAA GAATGTCTCC AAAACTTTGC CTGAATCTTT TGAATGAAGA ACTGGAAGAA   540
CTTAATATGA ATACAGAAA AATAGAAGAG GAATTTGAAA ATGCTGAAAA AGAACTTTTG   600
CACTACAAAA AAGAAATATT CACAAAACCC CTAAATTTTC AAGAAACAGA GACGGATGCT   660
TCAAAAAGTG ACTATGAACT TCAAGCTTTA AGAAATGACC TGTCTGAAAA AGCAACAAAT   720
GTAAAAAACT TAAGTGAACA GCTCCAGCAA GCCAAAGAAG TCATCCACAA ATTGAACCTA   780
GAGAACAGAA ATTTAAAAGA AGCTGTTAGG AAGTTAAAGC ATCAAACCGA GGTTGGAAAT   840
GTGCTCCTAA AAGAAGAAAT GAAATCATAT TATGAATTAG AAATGGCAAA GATCCGCGGA   900
GAGCTCAGTG TCATCAAGAA TGAACTGAGA ACTGAGAAGA CCCTACAAGC AAGAAATAAC   960
AGAGCCTTGG AGTTGCTTAG AAAATACTAT GCTTCTTCAA TGGTAACATC ATCAAGTATC  1020
CTTGACCACT TTACTGGGGA TTTTTTTTAA AACTTAAAAA AATCCTTCCA GTAGGCAAGT  1080
CATTGAGCCA AATCAGTGTT TATTGTATTT TCTTTGCGTA TTACTTAAAA TATATGTAAT  1140
AGGATGTTAT TTTCATTTTC AGTAAATCAC AGTATCTATA AACATATAC ATGTTTCCAA   1200
GCTTCTGCTT TCTCTTTCTG ATGAAGTTAT TGCAGGAATA CAAATGGAAA CGAAGCTTTG  1260
GAAATCTCAT ATCAGAGTGT GTGTGTGTGT GTGTGTGTGT GTGTGTACAC ACACACATAT  1320
ATTCACTCAA AACACATAA TGATTCACCA AATCATTTAT GAATACAAAT CAGCAATTTT   1380
GTGATCTCGT AAGCAAATAT GTCTTTGGCA CGTGAATATT TTTCCATCTG TGTTCATTGA  1440
TGTTAACAAT AAAAATCTTG TTTATGTGTA TAAGCCTAAA AAAAAAAAA AAAAAAA      1497
```

(2) INFORMATION FOR SEQ ID NO:59:

(i) SEQUENCE CHARACTERISTICS:
        (A) LENGTH: 1050 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:59:

```
ACCAGCTCTA CTAAGACAAG ACATAAGAAA GAAATTTATG GAAAGAATGT CTCCAAAACT      60

TTGCCTGAAT CTTTTGAATG AAGAACTGGA AGAACTTAAT ATGAAATACA GAAAAATAGA     120

AGAGGAATTT GAAAATGCTG AAAAAGAACT TTTGCACTAC AAAAAAGAAA TATTCACAAA     180

ACCCCTAAAT TTTCAAGAAA CAGAGACGGA TGCTTCAAAA AGTGACTATG AACTTCAAGC     240

TTTAAGAAAT GACCTGTCTG AAAAAGCAAC AAATGTAAAA AACTTAAGTG AACAGCTCCA     300

GCAAGCCAAA GAAGTCATCC ACAAATTGAA CCTAGAGAAC AGAAATTTAA AAGAAGCTGT     360

TAGGAAGTTA AAGCATCAAA CCGAGGTTGG AAATGTGCTC CTAAAAGAAG AAATGAAATC     420

ATATTATGAA TTAGAAATGG CAAAGATCCG CGGAGAGCTC AGTGTCATCA AGAATGAACT     480

GAGAACTGAG AAGACCCTAC AAGCAAGAAA TAACAGAGCC TTGGAGTTGC TTAGAAAATA     540

CTATGCTTCT TCAATGGTAA CATCATCAAG TATCCTTGAC CACTTTACTG GGGATTTTTT     600

TTAAAACTTA AAAAAATCCT TCCAGTAGGC AAGTCATTGA GCCAAATCAG TGTTTATTGT     660

ATTTTCTTTG CGTATTACTT AAAATATATG TAATAGGATG TTATTTTCAT TTTCAGTAAA     720

TCACAGTATC TATAAAACAT ATACATGTTT CCAAGCTTCT GCTTTCTCTT TCTGATGAAG     780

TTATTGCAGG AATACAAATG GAAACGAAGC TTTGGAAATC TCATATCAGA GTGTGTGTGT     840

GTGTGTGTGT GTGTGTGTGT ACACACACAC ATATATTCAC TCAAAAACAC ATAATGATTC     900

ACCAAATCAT TTATGAATAC AAATCAGCAA TTTTGTGATC TCGTAAGCAA ATATGTCTTT     960

GGCACGTGAA TATTTTTCCA TCTGTGTTCA TTGATGTTAA CAATAAAAAT CTTGTTTATG    1020

TGTATAAGCC TAAAAAAAAA AAAAAAAAA                                     1050
```